US008357375B2

(12) United States Patent
Palma et al.

(10) Patent No.: US 8,357,375 B2
(45) Date of Patent: Jan. 22, 2013

(54) PROCESS FOR THE PREPARATION AND USE OF A BIVALENT VACCINE AGAINST MORPHINE-HEROINE ADDICTION

(75) Inventors: Benito Anton Palma, Mexico (MX); Philippe Leff Gelman, Mexico (MX)

(73) Assignee: Instituto Nacional de Psiquiatria Ramon de la Fuente Muniz, Mexico, D.F. (MX)

( * ) Notice: Subject to any disclaimer, the term of this patent is extended or adjusted under 35 U.S.C. 154(b) by 0 days.

(21) Appl. No.: 13/182,634

(22) Filed: Jul. 14, 2011

(65) Prior Publication Data

US 2011/0318381 A1 Dec. 29, 2011

Related U.S. Application Data

(62) Division of application No. 11/632,085, filed as application No. PCT/MX2005/000049 on Jul. 5, 2005, now Pat. No. 8,008,457.

(30) Foreign Application Priority Data

Jul. 7, 2004 (MX) ..................... PA/a/2004/006617

(51) Int. Cl.
*A61K 39/385* (2006.01)

(52) U.S. Cl. .................................................... 424/194.1

(58) Field of Classification Search ........................ None
See application file for complete search history.

(56) References Cited

FOREIGN PATENT DOCUMENTS

| | | | |
|---|---|---|---|
| CN | 1196955 | | 10/1998 |
| WO | 92/03163 | A1 | 3/1992 |
| WO | 96/30049 | A2 | 10/1996 |
| WO | 98/14216 | A2 | 4/1998 |
| WO | 2004/076677 | A2 | 9/2004 |

OTHER PUBLICATIONS

Anton et al (Vaccine, 24:3232-3240, 1996).*
Wainer et al (Science 176:1143-1145, 1972).*
Akbarzadeh, Azim et al., "Design and synthesis of a morphine-6-succinyl-bovine serum albumin hapten for vaccine development," Biotechnol. App. Biochem., vol. 30:139-145 (1999).
Carrera, M. Rocio A. et al., "A second-generation vaccine protects against the psychoactive effects of cocaine," PNAS, vol. 98(4):1988-1992 (2001).
Gebhart, G.F. et al., "Morphine-6-Hemisuccinate as a Narcotic Analgesic," Life Sciences, vol. 18:829-836 (1976).
Heading, Christine E., "TA-CD Xenova," IDrugs, vol. 5(11):1070-1074 (2002).
Nestler, Eric J., "Molecular mechanisms of drug addiction," Neuropharmacology, vol. 47:24-32 (2004).
Pierce, "TFCS," retrieved online at http://www.piercenet.com (1998).
Wainer, Bruce H. et al., "Morphine-3-Succinyl-Bovine Serum Albumin: An Immunogenic Hapten-Protein Conjugate," Science, vol. 176(4039):1143-1145 (1972).
International Search Report for Application No. PCT/MX2005/000049, dated Jul. 11, 2006.
International Preliminary Report on Patentability and Written Opinion for Application No. PCT/MX2005/000049, dated Jan. 9, 2007.

* cited by examiner

*Primary Examiner* — Patricia A Duffy
(74) *Attorney, Agent, or Firm* — Nelson Mullins Riley & Scarborough LLP; Jill Gorny Sloper, Esq.; Jeanne M. DiGiorgio, Esq.

(57) ABSTRACT

The structural design, preparative methods and chemical composition of two structural formulations of bivalent vaccines against morphine-heroin addiction (morphine-6-hemisuccinyl-EDC-TFCS-tetanus toxoid and 3-O-carboxymethylmorphine-EDC-TFCS-tetanus toxoid), are disclosed. These vaccines are suitable for human use in which they are capable of triggering the synthesis of polyclonal antibodies against morphine opiate and its structural analogue, heroin, through the repeated in vivo administration of these formulations, in active vaccination protocols, in preclinical studies in rodents. The active vaccination paradigm through which these immunogens trigger a humoral immune response consolidated with a long-term immunological memory, characterized by the presence of high titers of specific antibodies against these two drugs of abuse, is also disclosed. Furthermore, the present invention reveals the efficacy of these conjugate formulations for triggering a sustained immunoprotection against morphine and heroin addiction using an intravenous self-administration paradigm of these two opiate substances in the rodent. Finally, a discussion is also made on the potential future use of these immunoconjugates in active vaccination protocols for treating both morphine and heroin addiction in the humans.

14 Claims, 13 Drawing Sheets

Morphine

Succinic anhydride

Morphine-6-hemisuccinate

EDC

EDC-(Morphine-6-hemisuccinate)
intermediate derivative

CP-TFCS complex

EDC-(morphine-6-hemisuccinate)

Byproduct (Urea)

CP-TFCS complex

Intermediate EDC-(3-O-Carboxymethylmorphine)

Byproduct (Urea)

PROCESS FOR THE PREPARATION AND USE OF A BIVALENT VACCINE AGAINST MORPHINE-HEROINE ADDICTION

RELATED APPLICATIONS

This application is a divisional application of U.S. patent application Ser. No. 11/632,085, filed on Jan. 17, 2008, which claims the benefit of and which is a national stage filing of International Application Serial No. PCT/MX2005/000049, filed on Jul. 5, 2005, which claims priority to, and the benefit of, Mexican Patent Application Serial No. PA/A/2004/006617, filed on Jul. 7, 2004, the entire contents of both of which are hereby incorporated by reference.

The present invention received support and scientific advice from Dr. Gerardo Heinze Martin and Dr. Ramón de la Fuente Muñiz. Work funded by the Fundacion Gonzalo del Rio Arronte and the Instituto Nacional de Psiquiatría Ramón de la Fuente Muñiz (Grant 2040).

TECHNICAL FIELD

The present invention discloses a process for the preparation and use of a bivalent vaccine against morphine-heroin addiction, which is capable to induce a robust humoral immune response against these two addictive opiate drugs through the active immunization in mammals including the human. The process for the preparation of such bivalent vaccine consists in its design, synthesis, purification, application and therapheutic validation. The structural formulation of this vaccine consists of the initial synthesis and haptenization of a morphine-6-hemisuccinate intermediate derivative to the tetanus toxoid used as carrier protein. This latter chemical step is carried out using a long spacer linker arm sequentially synthesized from the covalent condensation of the homobifunctional cross-linker reagent, the 1-ethyl-3-(3-dimethylaminopropyl)carbodiimide (EDC) and the heterobifunctional cross-linker reagent N-(ϵ-trifluoracetylcaproyloxy)-succinimide-ester (TFCS). The humoral immune response induced by active immunization with such vaccine was characterized by the presence of very high and sustained titers of circulating polyclonal antibodies that recognize and bind with equivalent specificity both morphine and heroin in the blood, thereby preventing its blood-brain barrier permeation into the brain. The altered pharmacokinetics of these two drugs leads to a significant reduction of the "free" unbound fraction of morphine and heroin in plasma, thereby blunting drug entry into the brain. Thus, the antibody antagonism on the brain barrier permeation of opiates enhances an immunoprotective mechanism that blunts the drug-reinforcing effects of these two opiate substances acting on the mesocorticolimbic reward pathway, in actively vaccinated rodents with this immunogen previously trained to self-administered these two pharmacological reinforcers. Therefore, the present invention describes the process for the preparation of a bivalent vaccine against morphine/heroin addiction which represents a new immunoreagent or pharmaceutical composition or therapeutic formulation that can be applied, evaluated and validated as a new anti-addictive immunopharmacological therapy against these two opiate drugs in active vaccination protocols in humans.

BACKGROUND OF THE INVENTION

The abuse of illegal substances with reinforcing addictive properties represents a major public health problem worldwide. For instance, in the United States of America, nearly 48 million people have been exposed to illegal drugs over a one-year period (Neurobiological Adaptations to Psychostimulants and opiates as basis of treatment development. In: New Medications for Drug Abuse, K. Severino, A. Olivito and T. Kosten, 2000). Thus, this health problem has serious and progressive deleterious effects on social, economic and medical areas in affected countries. Epidemiologically, the pyschostimulants such as cocaine and amphetamines, and to a lesser extent, opiate substances, like heroin and morphine, represent the most prevalent drugs causing the highest addictive morbidity worldwide. In developing countries like Mexico, the epidemiological data from the latest National Survey of Addictions (M. E. Medina-Mora and E. Rojas Guiot, Salud Mental, 26(2): 1-11, 2003) reported an alarming increase in the drug-intake of such substances in the central part of the country as well in cities located between Mexico and US border. At the clinical level, there are several co-morbid pathologies related to the addictive abuse of illegal substances, which fall into different categories. Firstly, the high death index related to the toxic effects induced by the overdose of such substances. Secondly, the induction of teratogenic effects in the newborn, which are frequently associated to the chronic abuse of illegal substances by addicted pregnant mothers. Finally, the high incidence of co-morbid diseases of acquiring viral infections such as the human immunodeficiency virus (HIV), frequently detected in heroin abusers, as well as the increased rates of crimes, violence and delinquency frequently associated to the drug-trade and drug-intake of such illegal substances. Thus, at the therapeutical level, there exist an urgent need to refocuse and establish straightforward goverment strategies, health programs and novel medications to fight efficiently against drug abuse to illegal substances.

The neurobiology of drug addiction began more than three decades ago and most of investigations have dealt with drugs' pharmacokinetics and pharmacodymamics. At the pharmacokinetic level, illegal substances of abuse such as cocaine, morphine and heroin, exhibit potent drug-reinforcing properties and specific pharmacokinetic profiles, which ultimately lead to their high addictive drug effects in the brain. Morphine is an alcaloid with a phenantrenic chemical structure (see example 1) obtained from the milky extract (opium gum) of the *Papaver somniferum*, and represents the main compound extracted (≧10%) together with other structurally-related compounds such as codeine, tebaine, and papaverine (C. P. O'Brien, Drug Abuse, In: The Pharmacological Basis of Therapeutics. Pp. 621-642, $10^{th}$ ed. J. G. Hardman and L. E. Limbird, eds. McGraw Hill, New York, 2001). Morphine possesses a hydroxyl group in the third position and an alcoholic hydroxyl group in the sixth position placed within the phenolic ring structure. Conversely, heroin, a semi-synthetic derivative of the morphine, has two acetyl groups condensed in the aforementioned positions within the opiate phenantrenic ring structure (C. P. O'Brien, Drug Abuse, In: The Pharmacological Basis of Therapeutics. pp. 621.642, $10^{th}$ ed. J. G. Hardman and L. E. Limbird, eds. McGraw Hill, New York, 2001). Both morphine and heroin are absorbed from the gastrointestinal and respiratory tract, including oral mucosa, as well as from the subcutaneous, intramuscular, intravascular and intrathecal spaces. These two opiate compounds display a striking similar pharmacokinetic profile, based on their high blood-brain barrier permeation capability, mostly due to their high lipophilic properties (C. P. O'Brien, Drug Abuse, In: The Pharmacological Basis of Therapeutics. pp. 621-642, $10^{th}$ ed. J. G. Hardman and L. E. Limbird, eds. McGraw Hill, New York, 2001). In fact, heroin is relatively more lipophilic than morphine and thus permeates faster the blood-brain barrier than morphine. The main catabolic route of morphine mainly occurs in the liver and depends on enzymatic-dependent conjugation with glucuronic acid at both the three and six hydroxyl groups placed at the phenantrenic ring structure, producing endogenous metabolites compounds, such as morphine 3-, morphine 6-, and to a lesser extent, morphine 3-6-glucuronide. These catabolic intermediate compounds, represent the structural secretory and/or excretory forms of morphine in the urine. Moreover, morphine-6-glucuronide has been shown to display a potent analgesic and psychotropic, drug-reinforcing effects in the brain. Thus, morphine metabolites generated from the liver into the bloodstream, rapidly permeate the blood-brain barrier and activate the mu opioid receptor subtype in the brain reward pathways mediating the reinforcing effects of drug of abuse (L. M. Kamendulis et al., J. Pharmacol. Exper. Ther. 279:713-717, 1996; C. W. Hutto Jr. y W. Crowder, Pharmacol. Biochem. Behav. 58(1):133-140, 1997; A. J. Halliday et al., Life Sci. 65(2)225-236, 1999 and D. E. Selley et al., Biochem. Pharmacol. 62:447-455, 2001). In fact, recent pharmacokinetic studies (see review and references therein in J. Halliday et al., Life Sci. 65(2)225-236, 1999) support the idea that the analgesic and/or addictive actions of morphine in CNS are not directly and predominantly mediated by morphine itself, but largely exerted by its glucuronated active metabolites such as the morphine-6-glucuronide. So far, several studies (L. M. Kamendulis et al., J. Pharmacol. Exper. Ther. 279:713-717, 1996 and A. J. Halliday et al., Life Sci. 65(2)225-236, 1999) have shown similar pharmacokinetic and pharmacodynamic mechanisms for heroin. Thus, once heroin is administered, a large fraction of the drug is rapidly catabolized in the plasma and/or liver into 6-monoacetyl-morphine, and subsequently catabolized into morphine and finally converted into morphine-6-glucuronide, before reaching their neuronal targets (e.g., mu opioid receptor) (R. E. Aderjan and G. Skopp, Ther. Drug Monit., 20(5): 561-9, 1998). These findings support the current concept that the pharmacological agonism of heroin and its endogenous metabolites (e.g., 6-monoacetyl-morphine and morphine) on the mu opioid receptor including the final biotransformation active metabolites (e.g., morphine-6-glucuronide) represents the pharmacodymamic mechanism by which these substances enhance their reinforcing addictive actions in the brain (a. J. Halliday et al., Life Sci. 65(2): 225-236, 1999, D. E. Selley et al., Biochem. Pharmacol. 62:447-455, 2001 and C. P. O'Brien, Drug Abuse, In: The Pharmacological Basis of Therapeutics. pp. 621-642, $10^{th}$ ed. J. G. Hardman and L. E. Limbird, eds. McGraw Hill, New York, 2001).

Several pharmacodymic studies (see reviewed works in E. J. Nestler, Nat. Neuroci. 5:1076-1079, 2002 and P. N. Deslandes et al., J. Pharmacy and Pharmacol. 54:885-895, 2002) have shown that chronic abuse to both heroin and morphine leads to the development and establishment of specific long-term changes at the cellular and molecular level that ultimetaly produces the expression of biological neuroadaptations to opiate addiction. Moreover, these neuronal changes produce important electrophysiological, neurochemical and genomic changes, which are progressively established and consolidated upon a long-term period (e.g., years) in the brain during drug addiction. Therefore, the behavioral changes occurring during opiate addiction to these substance of abuse in the individual, follow a time-course of increased complexity and intensity with regard to the drug addiction symptomology. For instance, the repetitive administration of heroin by an addict, produces an increase stereotyped compulsive behaviors leading to uncontrolled drug-intake behaviors, associated with stereotyped rites of administration, initially accompanied by pharmacological tolerance and subsequently by physical signs and symptoms of drug withdrawal after acute suppression of the opiate drug (K. Severino et al., Ann. NY Acad. Sci 909: 51-87, 2000). Thus, heroin-intake behavior becomes the highest priority and necessity in the addicted individual, leading to the reinstatement of compulsive drug-intake and drug-seeking behaviors normally observed during drug withdrawal or abstinence. The neuroadaptative changes occurring during opiate addiction is primarily caused by the pharmacological actions displayed by the repetitive exposure of the drug over a clustered group of neurons localized in different areas of the brain (K. Severino et al., Ann. NY Acad. Sci 909: 51-87, 2000). These brain areas include the locus coeruleus, hippocampus, lateral hypothalamus, ventral-tegmental area, amygdaloid complex, nucleus accumbens and prefrontal cortex, which structurally comprised the neuroanatomical substrate and neural pathways where opiate substances and other illegal drugs of abuse (e.g., cocaine) mainly exert their drug-rewarding and drug-reinforcing activities (K. Severino et al., Ann. NY Acad. Sci 909: 51-87, 2000). In this context, the chronic administration of both morphine and heroin induces the development of a series of homeostatic cellular and molecular adaptative responses on neurons within the aforementioned brain structures impinged by the drug. Such adaptative responses involve several electrophysiological, biochemical and genomic alterations seen during drug addiction, which altogether, are produced to maintain and restore the pre-existing functional homeostasis of the implicated neural circuits and their operant neurons altered during drug abuse, prior to the compulsive drug-intake behavior (K. Severino et al., Ann. NY Acad. Sci 909: 51-87, 2000). Once these neuroadaptations have been established, the abrupt suspension of the drug-intake behavior enhances the development of new series of neurobiological changes and cellular adaptations in the neurons impinged by the drug, leading to the neuropathological basis that underlies the withdrawal syndrome during drug addiction. The withdrawal syndrome produced by both morphine and heroin in the addicted individual, as opposed to the withdrawal syndrome induced by cocaine and amphetamine, is characterized by highly intense physical and psychological alterations in the addicted individual (H. Ghodse, Drugs of abuse and dependence. In: Drugs and Addictive Behavior, a guide to treatment, Blackwell Science Ltd, ed., Oxford, UK, pp. 72-119, 1995; G. F. Koob, Ann. N.Y.: Acad. Sci. Vol. 909:185 2000 and K. Severino et al., Ann. N.Y. Acad. Sci 909: 51-87, 2000). Clinically, the withdrawal syndrome is characterized by four different stages developed in a progressive or gradual time-course. During the first 1-7 hours, the addict under abstinence develops behavioral manifestations characterized by a compulsive craving and extreme anxiety for drug-intake. During a second stage (after 8-15 hours), physical alterations such as intense lacrimation, extreme sweating, rinorrhea and lethargy are added to the initial drug symptomology. Further on, after 16-24 hours upon continuing drug withdrawal, physical signs such as mydriasis, piloerection, muscular cramps and changes in body temperature (e.g., intense cold and heat perception) in addition to diffuse algias, anorexia and irritability may appear as well. Subsequently, upon pesistent withdrawal (e.g., 2-6 days), other physical and behavioral signs may appear which include insomnia, fever, motor delay, abdominal pain, vomiting and diarrhea as well as increased abnormal breathing, including changes in pulse frequency and blood pressure. Thus, from the perspective of symptomology occurring in drug addiction, the duration and severity of morphine and heroin withdrawal depends on several pharmacokinetic and pharmacodynamic factors. Moreover, there has been reported that the severity of opiate withdrawal syndrome depends on several pharmacological and biological aspects, which include the daily amount of drug-intake (e.g., dose injected by the individual), the period of time of drug use and/or abuse, in addition to the physical and personality status of the individual affecting drug-intake response.

Thus, given the complexity of the natural history of the morphine/heroin addictive pathology, few currently available pharmacological treatments have been designed to modify the pharmacodynamic mechanisms by which these opiate substances produce their drug-reinforcing actions once they bind their specific receptor sites at their targeted neurons (D. M. Grilly, Opioids (narcotics) and their antagonists. In: Drugs and human behavior, $4^{th}$ ed. pp. 238-262, Allyn and Bacon, eds. USA, 2002). In this context, the acute opiate detoxification treatment represents the initial and most currently used pharmacotherapeutic approach to treat clinically chronic addicts, which becomes a medical priority and emergency to relieve the individual's physical signs and symptoms of drug withdrawal, which are commonly associated with physiological, endocrinological and chemical disturbances induced by drug addiction. For example, mu opioid receptor partial agonists such as methadone and buprenorphine, in combination with benzodiazepines and/or sedative neuroleptics are commonly prescribed and administered for the acute desintoxication treatment to opiates. As opposed to the acute detoxification procedures used to treat opiate addiction, the substitution therapy using opiate substances such as methadone and/or buprenorphine as well as opioid receptor antagonists, such as naloxone and/or naltrexone, are not entirely recommended during opiate withdrawal, because they exacerbate the demand of drug-intake behavior of the parent opiate compounds that elicited or installed the former drug addictive state in the individual. Under normal circumstances, the treatment and maintenance of opiate withdrawal syndrome requires hospitalization and clinical care with the support of specialized medical personnel, which commonly results to be highly expensive. Likewise to the withdrawal syndrome, the complete morphine and/or heroin detoxification (supression of drug-intake behavior) in addicted individuals is an important health issue to be pursued. Based on the wide range of abnormal functional changes established after a long-term period in the brain produced by chronic opiate abuse, it is easy to understand the difficulties to re-establish the homeostatic function of the brain, prior to drug-intake, by the current available detoxification therapies. Thus, despite these therapeutic limitations, an ideal detoxification treatment must be address to meet specific medical criteria described as follows. Firstly, it should be directed to block or blunt the physiological and psychological opiate dependence in order to re-establish the homeostatic balance of those neural systems chronically dysregulated by opiate substances. Secondly, the detoxification treatments should inhibit those pertinent physical and behavioral changes that appear to be exacerbated during drug withdrawal induced by therapeutic interventions, thereby resulting in a tolerable experience and safety treatments. Additionally, it should provide a complete suspension of the individual's drug-intake behavior, thus reorientating the addicted individuals to other alternate available non-pharmacological treatments (e.g., psychotherapy and counseling). Thereafter, once the complete opiate detoxification therapy is reached, the final medical goal to be approached is the prevention of subsequent relapses to opiate abuse. Thus, from a general medical viewpoint, the therapeutic challenges to blunt morphine/heroin addiction are enormous and, in most of cases, difficult to improve. The main obstacles faced by both pharmacological and non pharmacological-based treatments, are the lack of an adequate number of specialized clinics or hospitals, the high economical costs of therapy usually billed to the patient and, most importantly, the absence of either patient follow-up programs (i.e., years) or continuos clinical evaluation as wella as the lack of application of long-term psychotherapy support to prevent drug-relapse. In addition, another major problem facing most of the current anti-addictive treatments against opiate abuse is the side-effect toxicity resulting from long-term dosification of single or combined pharmacological agents (K. Severino et al., Ann. NY Acad. Sci 909: 51-87, 2000). For example, methadone and buprenorphine, two long-lasting partial agonist of the mu opioid receptor, represent the most common substitution therapeutic drugs used today to blunt opiate withdrawal syndrome or to prolong opiate abstinence (M. J. Kreek, Ann. N.Y. Acad. Sci, 909: 186-216, 2000). In addition, $\alpha_2$ adrenergic receptor agonists such as clonidine, guanfacine and/or lofexidine represent another set of compounds used quite frequently in detoxification therapies to amielorate withdrawal signs and symptoms caused by the abrupt supression of opiate drugs (M. J. Kreek, Ann. N.Y. Acad. Sci, 909:186-216, 2000). However, besides of their widely use in long-term detoxification therapies and/or treatment maintenance of abstinence, these drugs have been shown to induce several toxic side-effects. For example, methadone, buprenorphine and pentazocine have been reported to produce sleep disorders, anxiety and severe cognitive and emotional impairment. Additionally, $\alpha_2$ adrenergic receptor agonists have been reported to produce sedation, hypotension, extreme anxiety and asthenia upon long-term administration. In addition, patients receiving opiate-substitution with methadone, may not surprisingly, show the development of signs and symptoms of opiate-dependence due that this mu opioid receptor partial agonist produces same neurochemical, cellular and molecular neuroadaptative changes in the brain, as those reported for both morphine and heroin during opiate addiction (M. J. Kreek, Ann. N.Y. Acad. Sci, 909:186-216, 2000). Other available drugs currently used to prolong abstinence and to relapse prevention against morphine/heroin addiction in detoxified patients comprise the mu opioid receptor antagonists, naloxone and naltrexone. The toxic side effects often seen during the long-term administration of these compounds are mostly due to the blockade of the endogenous opioid transmission systems in the brain, leading to impairement of both cognitive and emotional brain functions, among many other physiological activities (M. J. Kreek, Ann. N.Y. acad. Sci, 909:186-216, 2000).

Thus far, one major conclusion drawn from the above described pharmacological therapies currently used to approach detoxification against opiate abuse including long-term maintenance treatments for drug-withdrawal and relapse-prevention against morphine/heroin addiction, is that none of these pharmacological treatments have shown an optimum efficacy. This conclusion is based on the fact that these drugs produce important toxic side-effects in patients receiving long-term maintenance of abstinence and/or relapse-prevention (T. Kosten and D. Biegel, Expert Rev. Vaccines, 1(3): 89-97, 2002). Thus, there is an urgent need to develop and validate novel anti-addictive therapeutic strategies, based on the synthesis, application and validation of highly effective new drug formulations, displaying minimum toxicity and no detected side-effects, when pretend to be use in the long-term therapies for acute detoxification and long-term maintenance of morphine/heroin abstinence.

For this reason, here are given and shown all the reports and documents concerning the state of the art of the development and application of techniques related to the present invention, which are detailed herein and are also included to be used only as reference material.

In this context, different groups have designed, applied and validated alternative therapeutic strategies in experimental animal models, which share a common pharmacokinetic mechanism. Thus, conversely to the classical anti-addictive pharmacology, this latter mechanism is based on altering the drug's pharmacokinetics by decreasing significantly or blunting the blood-brain barrier permeation of the "free" unbound drug in plasma, which ultimately represents the fraction of drug in plasma that permeates the brain causing the high reinforcing and rewarding effects in the addicted individual. All of these experimental approaches have been focused to decrease significantly or prevent the blood-brain barrier permeation of drugs of abuse, by enhancing the binding of the "free" unbound fraction of drug in plasma by specific antibodies, which recognize and bind with high specificity and avidity to these drugs in the blood. As immunoglobulins (antibodies) do not normally permeate the blood-brain barrier, the plasma fraction of "free-unbound drug", which is the available pool of drug that permeate the blood brain barrier, interact with immunoglobulins establishing drug-antibody complexes, which ultimaltely decreases significantly this fraction of free-unbound drug in plasma. This change in the drug's pharmacokinetics in plasma, leads to altered changes in drug's pharmacodynamics in the brain, thus blunting or abolishing the activity of addictive drugs on their specific targeted neurons. These latter pharmacodynamic changes ultimately lead to blunt both the development of the reinforcing activities and the rewarding pleasant effects induced by drugs of abuse in the brain. The main pharmacokinetic property shared by most drugs of abuse, is the high blood-brain permeation activity, which represents the basic and crucial mechanism, by which most of the potent drugs of abuse produced their highly intense reinforcing actions in the brain, leading to the continous drug-intake and drug-seeking behaviors display by individuals upon exposure to these chemical compounds. In this context, the generation of specific serum antibodies against drugs of abuse represents an alternate therapeutical approach to blunt or prevent the blood-brain barrier permeation of drugs of abuse from reaching its neuronal targets. This antibody antagonism approach preventing drug's permeation into the brain has been shown to enhance an immunoprotective effect against drug-intake and drug-seeking behaviors, as demonstrated for cocaine, nicotine, PCP and amphetamines in rodents (see an account of reviewed works and references therein in T. Kosten and D. Biegel, Expert Rev. Vaccines, 1(3): 89-97, 2002 and K. Kantak, Drugs, 63(4): 342-252, 2003). With regard to cocaine, several research groups were able to develop and apply different experimental strategies based on the design, synthesis, application and validation of several immunogenic preparations of carrier proteins with covalently haptenized cocaine (Kantak et al., Psychopharmacology 148:251-262, 2000; Fox, B. S. et al., Nat. Medicine, 2:1129-1132, 1996; Sparenborg et al., Therapeutics 293(3): 952-961, 2000; Carrera et al. Nature, 378:727-730, 1995, Carrera, R. et al., Proc. Nat. Acad. Sci, USA, 97(11)6202-6206, 2000). Some high molecular weight proteins such as BSA and KLH have been used as carriers to covalently link cocaine using standard chemical covalent coupling procedures. In this way, following active immunization protocols in rodents, some of these immunogens have shown capabilities to generate low to moderate antibody titer responses against this drug of abuse in actively vaccinated animals. Moreover, other experimental approaches conferring immunoprotective effects against cocaine addiction have been explored by enhancing the generation of conventional and/or catalytic monoclonal antibodies administered during passive immunization protocols against this psychoactive drug in rodents (Metz et al., Proc. Natl. Acad. Sci. USA 95:10176-10180, 1998; Fox et al., Nat. Med. 2:1129-1132, 1996 and Landry et al., Science, 239: 1899-1901, 1993). The immunoprotective effects against cocaine addiction using these immunological-based experimental strategies have been explored by detecting the abolishment of the drug-reinforcing behaviors in rodents in combined pharmacological and operant-behavioral paradigms. These experimental strategies share a common anti-addictive mechanism, which relies in the significant reduction and/or complete inhibition of the blood-brain permeation of the "free" unbound fraction of cocaine in plasma. Thus, in actively vaccinated hyperimmune animals, the fraction of "free" unbound of drug in plasma is significantly reduced, once specific serum antibodies in the blood bind to the psychoactive drug (Kantak et al., Psychopharmacology, 148: 251-262, 2000; Carrera et al., Proc. Natl. Acad. Sci. USA, 97(11):6202-6206; Carrera et al., Nature, 378:727-730, 1995). Alternatively, monoclonal antibodies raised against cocaine, may bind the "free" unbound fraction of cocaine after being passively transferred into the blood (Metz et al., Proc. Natl. Acad. Sci. USA 95:10176-10180, 1998; Fox et al., Nat. Med. 2:1129-1132, 1996, Benowitz, Pharmacol. Toxicol. 72:3-12, 1993). In both cases, the common immunological neutralizing mechanism, which promotes altered changes in cocaine pharmacokinetics, leads to the significant decrement or complete inhibition of drug's entry into the brain, thereby decreasing or blunting the targeting of cocaine to the specific neuronal membrane dopamine reuptake transporter. This latter antibody-mediated mechanism inducing altered changes in cocaine's pharmacodynamic in the brain, would lead to changes in the synaptic level of amine neurotransmitters, abolishing the evoked-dependent increase in the central catecholaminergic tone, normally seen after cocaine's entry into the brain in addictive individuals. The final behavioral scenario that results from these altered changes in cocaine pharmacokinetics and neurochemical events is the lack of the intensified rewarding effects induced by this potent reinforcing drug in the brain of mammals. Thus, once cocaine has been neutralized to produce its reinforcing and rewarding effects in hyperimmune animals, the reinforcing properties of this drug will be lost upon a subsequent drug exposure, as demonstrated by the supression of drug-seeking and drug-intake behaviors in such hyperimmune vaccinated animals (rodents) seen with use of some immunogenic conjugates of cocaine.

In summary, most of the aforementioned pre-clinical studies have shown the feasibility of using antibody-based antagonism approach for blunting drug-taking and drug-seeking behaviors in rodents. However, the type of the carriers proteins (e.g., BSA and KLH) used in the preparation of the immunogenic conjugates (vaccines) used in these studies preclude its potential use in vaccine formulations for use in human immunization protocols (Carrera et al., Proc. Natl. Acad. Sci. USA, 2001; Carrera et al., Proc. Natl. Acad. Sci. USA, 2000; Carrera et al., Nature, 378:727-730, 1995; Kantak et al., Psychopharmacology, 148:251-262, 2000; Ettinger et al., Pharmacol. Biochem. Behav. 58:215-220, 1997 and Fox, Drug and Alcohol Depend. 48:153-158, 1997). Furthermore, the synthesis of conventional andor catalytic mouse anti-cocaine monoclonal antibodies used as potential passive immunotherapy for addition in experimental animals (rodents), has the main limitation in conferring immunoprotection in a short-term period when passively administered. This is mostly due to the fast metabolic clearance of these murine immunoglobulins from serum of passively immunized animals other than mice (Goldsby et al., Vaccines, In: Kuby Immunology, $4^{th}$ ed. Freeman and Co. New Cork, N.Y., pp. 449-466, 2000). Moreover, the potential use of the available murine anti-cocaine monoclonal antibodies as immunological therapeutic agents against cocaine addiction in humans, requires the use of DNA recombinant techniques, so as to "humanize" the Fc segment of murine immunoglobulins.

Finally, the potential application of this antibody-based antagonism against cocaine addiction in the human is a current issue under experimentation as a therapeutical approach. This immunopharmacological strategy was initially approached through the synthesis of an anti-cocaine vaccine formulation, structurally designed for human use, where cocaine was covalently conjugated to the recombinant β-subunit of the cholera toxin (used as carrier protein. At preclinical level, this conjugate showed moderate efficacies in triggering antibody responses in actively vaccinated rats that confered immunoprotective effects to prevent relapse to cocaine taking-behavior in this animal (Kantak et al., Psychopharmacology, 148:251-262, 2000). Additionally, active vaccination with this immunogen in human volunteers, used to test the safety and immunogenicity of this vaccine formulation, unfortunately, showed little promissory therapeutic effects, in this single Clinical Phase I study (T. Kosten et al., Vaccine 2559:1-9, 2001), due to the fact that this vaccine formulation showed a poor immunogenic capacity, producing low antibody titer responses [e.g., low concentration range (μg) of specific immunoglobulin/ml of serum] in most of the vaccinated subjects. In addition to the aforementioned experimental limitations, new anti-cocaine vaccines developed by different groups of research, are currently being under study, using different carrier proteins, in order to generate an improved immunogenicity against this psychoactive drug in both pre-clinical and Clinical Phase I studies. Once the immunogenic properties of these vaccine formulations are validated in humans in Clinical Phase I studies, it may become available for a subsequent evaluation in Clinical Phase II studies assessing the immunoprotecting capabilities of these vaccine formulations against cocaine addiction. For instance, it could be used Clinical Phase II studies by assessing the enhanced long-lasting humoral-based immunoprotection against cocaine addiction, in former drug addicts, exhibiting a prolong and controled abstinence but challenged to the pharmacological reacquisition of addictive cocaine-intake behavior.

In the case of tobacco addiction, at least two immunogenic preparations (vaccines) to the reinforcing psychoactive substance, namely nicotine, have been designed for human application (see an account of reviewed works and selected references therein in T. Kosten and D. Biegel, Expert Rev. Vaccines, 1(3): 89-97, 2002; K. Kantak, Drugs, 63(4): 341-352, 2003). Pre-clinical studies have demonstrated that these two vaccines were able to generate low to moderate serum titers of specific antibodies (i.e., 0.05-0.2 mg/ml of serum) against nicotine in actively vaccinated rodents. Moreover, active vaccination with these immunogenic preparations of nicotine, demonstrated to confer immunoprotection against the acquisition nicotine-intake behavior in intravenous drug-self-administration paradigms in rodents. The immunoprotective mechanism against nicotine addiction follows same pharmacokinetic mediated-mechanism described for cocaine addiction, that is, through the binding of the "free" unbound fraction of nicotine in plasma by specific serum antibodies, which prevents the blood-brain barrier permeation of this drug. Clinical Phase studies performed independently by Nabi Pharmaceuticals (Anti-nicotine vaccine NicVAX) and Xenova Pharmaceutical Group in Belgium, reported successful results on the evaluation of the toxic and immunogenic properties of these two vaccine formulations. The reports on the evaluation of the immunoprotection capabilities of these two vaccine formulations against nicotine addiction in former drug addicted volunteers in Clinical Phase II studies are expected to be ready in the next two coming years.

In fact, the development of experimental strategies focused in the design and synthesis of immunogenic preparations and the subsequent validation of vaccination protocols for treating specific forms of drug addiction, were pioneered approached for opiates such as morphine and heroin, but not for cocaine and nicotine addiction. Retrospectively, at the beginning of the 70s, different research groups showed the feasibility of raising a humoral immune response against these two opiate substances using vaccination protocols in experimental animal models, such as the rat and the rabbit (S. Spector and C. W. Parker, Science, 168:1347-1348, 1970; S. Spector, J. Pharmacol. Exp. Ther. 178:253-258, 1971; E. L. Adler and C. Liu, J. Immunol, 106:1684-1685, 1971; H. Van Vunakis et al., J. Pharmacol. Exp. Ther. 180:514-521, 1972; B. H. Wainer et al., Science, 176-1143-1145, 1972; B. H. Wainer et al., Science, 178:647-648, 1972 and B. H. Wainer et al., J. Immunol. 110:667-673, 1973). These experimental approaches were focused in generating polyclonal antibodies against morphine, displaying distinct immunological cross-recognition against heroin and structurally related opiate analogues (e.g., codeine, meperidine, and hydromorphone). These antibodies were generated for using in specific-designed immunoassays (i.e., radioimmunoassay and ELISA immunoenzymatic assays) to detect and measure morphine and related opiate substances in biological fluids from humans. These studies showed, for the first time, the successfull achievement on the design and validation of the covalent condensation of the exposed free 3- and 6-hydroxyl groups in the phenantrenic ring of the morphine molecule to carrier proteins such as BSA, using standard organic chemistry procedures (procedures that are still used when approaching chemical synthesis of such immunogenic conjugates). In addition, it is worth to mention that none of these chemical procedures were never reported and claimed in patent registries and they are mostly considered as classical chemical procedures in textbooks of organic chemistry, when describing the covalent linkage of the free 3- and 6-hydroxyl groups of the phenantrenic ring of morphine to carrier proteins. In such context, two structural intermediate products from morphine were sucessfully synthesized by different research groups and used for the development of vaccine formulations, namely, the 3-ortho-morphine-carboxymethyl-ether product (3-O-carboxymethylmorphine, see example 2) and the morphine-6-hemisuccinate (see example 3) (S. Spector and C. W. Parker, Science, 168:1347, 1970; S. J. Spector, J. Pharmacol. Exp. Ther. 178:253, 1971; H. Van Vunakis et al., J. Pharmacol. Exp. Ther. 180:514, 1972; and S. Gross et al., Immunochemistry, 11:453-456, 1974). With regard to the aforementioned intermediate derivaties of morphine used to develop vaccine formulations, two identical patent registries published on Sep. 13, 1991 (CH 678394 A5) and May 15, 1996 (EP 0 496 839 B1) by Erich Hugo Cerny, claim invention on the structural synthesis of novel anti-morphine vaccine formulations. However, it's worth to mention, that both of these patent registries reveal no real novelty or invention regarding the synthesis of the therapeutic vaccine formulations claimed. This argument is based on that both patent registries describe the same standard synthetic procedures previously reported to generate the intermediate 3-O-carboxy-methyl-morphine derivative used to covalently conjugate the KLH-carrier protein. In both instances, they used morphine-based and the sodium beta-chloroacetate and absolute alcohol as reagents in the reaction mixture. The other synthetic intermediate derivative used to activate the covalent linkage between morphine and carrier proteins, is the morphine succinyl ester linked to the free 6-hydroxyl group of the phenantrenic ring-structure of the morphine molecule, namely, morphine-6-hemisuccinate, (see example 3) (originally reported by B. H. Wainer et al., Science, 176:1143, 1972, A. Akbarzadeh et al., Biotechnol. Appl. Biochem, 30:139-145, 1999). In same context to the aforementioned synthetic procedures used to generate the 3-O-carboxymethylmorphine derivative for synthetizing vaccine formulations, an anti-morphine vaccine patent registry released from China (CN1196955), was unjustified granted from our own perspective, to Han Ying et al., on Oct. 28, 1998. These authors claim innovation and novelty regarding the synthetic procedures and the structural formulations of vaccine preparations to different opiate drugs, besides morphine, using same standard methods to synthetize morphine-6-hemisuccinate derivative, as previously reported (see in B. H. Wainer et al., Science, 176:1143, 1972, A. Akbarzadeh et al., Biotechnol. Appl. Biochem, 30:139-145, 1999). These authors used this intermediate derivative to haptenize morphine to BSA as carrier protein.

The structural design and synthesis of different immunogenic formulations, where morphine has been haptenized to carrier proteins such as KLH and BSA, represented the basis by which authors have invariably used chemical procedures to link covalently the intermediate derivatives of morphine 3-O-carboxymethylmorphine and morphine-6-hemisuccinate to these carrier proteins (as previously outlined in the experimental studies described above, including the aforementioned patent registries), using as cross-linker the homobifunctional chemical reagent, 1-ethyl-3-(3-dimethylaminopropyl) carbodiimide (EDC). The EDC reacts with the available free carboxyl groups exposed in either the 3-O-carboxymethylmorphine or morphine-6-hemisuccinate derivatives, thus forming the corresponding two O-acylurea by-products, which are chemically reactive to generate covalent amide bonds with the epsilon (ϵ)-amino groups in the lateral chain of lysine residues of either BSA or KLH (see example 4).

The aforementioned studies demonstrating the feasibility to generate a humoral immune response against morphine and its structural cognate semisynthetic opiate, heroin, led to a pioneer study reported nearly 30 years ago by Bonese (K. F. Bonese et al. Nature, 252:708-710, 1974). This study was in fact the pioneer report demonstrating that active vaccination with an immunogenic morphine conjugate in a single experimental animal, the non-human primate *Macacus rhesus*, was able to generate a protective humoral-mediated immune response that blunt the addictive self-administration behavior to heroin. The synthesis of this immunogenic conjugate was achieved by covalently haptenizing morphine to the BSA through a stable ester bond formed by the condensation of the succinic anhydride and the 6-hydroxyl group in the phenantrenic structure of the morphine molecule. The synthesized intermediate derivative, morphine-6-hemisuccinyl, was then covalently linked to the 1-ethyl-3-(3-Dimethylaminopropyl) carbodiimide (EDC) reagent, thus obtaining the complete immunogenic conjugate. The repeated subcutaneous injection of this immunogen into the primate triggered a humoral immunological response with specific morphine antibodies, which displayed cross-recognition for heroin. Additionally, the active vaccination approach with this conjugate demonstrated to be an effective procedure to blunt the re-acquisition of the intravenous self-administration behavior to heroin in this single primate, previously trained to self-administer different dose-units of this opiate. Although this pioneer report showed the first successful antibody-based antagonism procedure to blunt heroin-intake behavior in the primate, it was never patented and developed for clinical use. Similarly, no further experimental studies related to the design, synthesis and validation of further novel structural anti-morphine/heroin vaccine formulations using carrier proteins suitable for human vaccination were developed, basically due to the fact that BSA is not a licensed carrier protein for such experimental purposes. The main reason that these immunopharmacological studies were never approached in humans with suitable immunogens for morphine or heroin could be due, at leat in part, to the simultaneous and continuous development of other neuropharmacological agents used to treat morphine-heroin addiction. For instance, synthetic drugs that display weak and partial agonist activities on the mu opioid receptor (i.e., methadone and buprenorphine) and other drugs which display antagonist activities on opioid receptors (i.e., naltrexone and naloxone). All these drugs are currently used for preventing relapse to opiate addiction.

Based on the aforementioned reports of experimental vaccines against morphine/heroin addiction, which never approached human vaccination, preliminary experimental studies conducted by our research group served as a basis, for the development of the present invention of the bivalent vaccine formulation against morphine-heroin addiction. These experiments describe the design, synthesis and evaluation of the immunogenicity induced by different synthetized structural models of a new generation of vaccines against anti-morphine/heroin (B. Anton and P. Leff., 31$^{st}$ Annual meeting of the Society for Neuroscience. San Diego, Calif. Nov. 10-16, 2001). Such structural formulations of vaccines were intially synthetized by linking covalently the morphine-6-hemisuccinate (M-6-H) intermediate derivative with several carrier proteins such as BSA, KLH and the recombinant cholera toxin-β-subunit protein. These coupling reactions used standard crosslinking procedures for linking the morphine-6-hemisuccinate (M-6-H) intermediate derivative to the 1-ethyl-3-(3-Dimethylaminopropyl)-carbodiimide (EDC) reagent. These preliminary experimental data gathered from such studies made possible the identification of candidate carrier proteins for covalent haptenization of morphine. It is worth to mention that this work was only presented in a slide session at the aforementioned International Neuroscience Meeting.

Furthermore, it did not show any information concerning experimental data related to the design of the structural molecular models of immunogens, methodologies describing the synthesis, purification, application and dosification procedures of these new vaccines. Moreover, no references or descriptions of the validation of the anti-addictive effects against morphine-heroin were also made, which are disclosed in the present invention of the therapeutic bivalent morphine-heroin vaccine formulation against the addiction to these opiate substances.

In addition to the pioneer study reported by Bonese and co-workers, who demonstrated the efficacy of the active vaccination with BSA-morphine to blunt the addictive self-taking behavior of heroin in a single primate, other research groups explored the immunoprotective effects of the passive immunization against morphine, using behavioral paradigms of intravenous self-administration of heroin in rodents (P. R. Pentel et al., Pharmacol. Biochem. and Behavior, 9:347-352, 1991). From a potential therapeutical viewpoint, a passive immunoprotection procedure against morphine and heroin addiction has practical limitations to prolong and maintain abstinence to opiate drugs in humans on a long-term basis, as opposed to the active immunization procedures. These limitations are based on some practical observations derived from experimental results of passive immunoprotection paradigms (R. A. Goldsby, Vaccines. In: Kuby Immunology, $4^{th}$ ed. Freeman and Co, New Cork, N.Y., pp. 449-466, 2001). These data have demonstrated the relatively short biological half-life of murine monoclonal antibodies (3-23 days, depending on the immunoglobulin class and isotype) after being administered in vivo into different experimental animals. Thus, immunoprotection conferred via passive administration of murine monoclonal antibodies into non-murine hosts is usually short-lived. Moreover, as both monoclonal and polyclonal antibodies used in passive immunization therapies are commonly produced from different animal species (e.g., mouse, rabbit, etc.), such immunoglobulins are usually recognized as foreign antigenic molecules when injected into human subjects. In this context, passive immunization of patients with such immunoglobulins would trigger a rapid humoral immunological response against these molecules, which ultimately result in a blunted antibody-mediated neutralizing responses and reduced half-life of these types of immunoglobulins in plasma. Thus, once primed such antigenic responses against heterologous antibodies in passively immunized subjects, the subsequent administration of these types of immunoglobulins would lead to the development of abnormal immunological responses of hypersensibility upon repeated passive administration of such molecules.

Aims and Advantages of the Invention

Based on the aforementioned background regarding the anti-addictive-based therapies against opiate abuse, specifically against morphine and heroin addiction, we can conclude that no efficacious and atoxic drugs are yet available in humans for treating and maintain prolong abstinence and relapse prevention from addictive opiate-intake behaviors. Thus far, reasons exist to justify the current need for the development, application and validation of combined new drugs and therapeutic strategies to maintain prolonged abstinence with efficacy for preventing relapse to addictive drug-intake behaviors to highly addictive opiate drugs such as heroin and morphine in the humans.

As previously mentioned, the previous experimental studies reporting the pre-clinical evaluation of different immunological strategies against drug addiction in animal models, support the potential therapeutic approach of the different immunoprotective strategies against cocaine, nicotine and opiate addiction (specifically to both morphine and heroin). This strategies include new pharmacological treatments based on antibody antagonism for the maintenance of prolong abstinence and/or prevention of relapse to drug intake and drug addiction to the aforementioned substances in the humans. In fact, the most important legacy of these immunoprotective studies against drug addiction, is the identification of the critical experimental achievements from both pre-clinical and clinical Phase studies, which ultimately would lead to the potential use and validation of these immunological strategies in humans to maintain prolong abstinence and/or to relapse prevention during addictive disorders to illegal drugs of abuse.

In this context, we can mentioned the following experimental requirements to be meet: a) design and synthesis of structural formulations of anti-addictive vaccines where the haptenic drug is structurally coupled via very stable covalent links (i.e., amide), using bifunctional chemical compounds with low structural complexity and immunogenicity that enhance the covalent crosslinking of the haptenic drug with licensed carrier proteins used in vaccination protocols in the humans; b) such proteins should display proven atoxicity, and should be able to confer a very high immunogenicity to the haptenic drug when the drug-protein conjugate is administered in active immunization protocols; c) systematic evaluation of the humoral immune response to the haptenic drug conjugated to the carrier protein, so that functional parameters of triggered specific antibodies such its titers, specificity and avidity can be properly characterized after application of the immunoconjugate in ad hoc active vaccination protocols; d) systematic monitoring of the humoral immune response during the active vaccination protocls with the immunogenic conjugate containing the haptenized addictive drug, so as to identify and assess the establishment of a long-term and stable humoral memory response against the antigenic drug after completion of the active immunization protocols; e) assessing of the capacity and efficacy of these new therapeutic vaccine formulations against drug addictions (i.e., morphine-heroin) with proven capacities to confer long-term immunoprotection against addictive drugs. These vaccines should exhibit a good therapeutic index to prevent the reacquisition of the addictive behaviors in detoxified and abstinent subjects.

The present invention relates to the design, synthesis, purification, application and validation of a novel structural model of vaccine against both morphine and heroin addiction, that fulfills all the aforementioned structural and functional requirements. The detailed description of the synthesis procedures and the structure of this carrier protein-morphine conjugate, are disclosed in the present invention. Other information also disclosed therein are its use in paradigms of active immunization in the rodent, the monitoring and characterization of the development of the humoral immune response after boosting, as well as the titers and the antibody specificity generated against the haptenized drug. Additionally, expefrimental data are also disclosed showing the proven efficacy of the present invention of the therapeutic formulation of a novel bivalent vaccine against morphine/heroin to induce a robust humoral immune response of high and sustained serum antibody titers against morphine, with equivalent specificity for heroin, in detoxified and abstinent subjects addicted to these opiate substances. Such antibodies can efficiently antagonize (block) the reacquisition of the addictive drug-intake and drug-seeking behaviors, in addition to prolong the abstinence state against these two opiate substances in hyperimmune subjects challenged to drug's reacquisition in a standard addictive intravenous self-administration paradigm of these two opiate substances in the rat.

The first aim of the present invention is to disclose the method of synthesis and the structural formulation of a novel morphine immunogen, which has the following functional and structural advantages never presented in any other previously synthetized morphine/heroin vaccine formulations: a) covalent morphine haptenization to the tetanus toxoid, a carrier protein licensed in active vaccination protocols in the human with proven capacity to confer a very high immunogenicity to hapten molecules of low molecular mass; b) covalent morphine haptenization to the tetanus toxoid, through the sequential use and covalent linkage of two different crosslinking reagents, which enhances the synthesis of a long and low immunogenic spacer linker-arm placed between the carrier protein and the haptenized drug; c) this novel morphine immunogen was dosified in active vaccination protocols in subjects, and showed a proven efficacy to generate a robust and sustained humoral immune response characterized by highly specific serum antibodies with equivalent specificities against morphine and its structurally related and highly addictive opiate analogue, heroin.

Another aim of the present invention is to disclose and validate an active immunization paradigm using the aforementioned carrier protein-morphine conjugate, for optimizing a robust and sustained humoral immune response with very high anti-hapten antibody titers with an established long-term immune memory response.

Another aim of the present invention deals with the demonstration for optimizating the antibody titer and specificity, in order to demonstrate its functional capacity for cross-recognizing heroin, but not other opiate medications structurally-related to morphine and/or several endogenous opioid peptides produced in the brain.

Another aim of the present invention concerns with the validation on the use of this immunogen, as a novel pharmaceutical composition or therapeutical formulation to confer immunoprotection against the re-acquisition of addictive morphineheroin-intake behaviors and for the maintenance of prolonged abstinence in experimental subjects previously detoxified from either morphine or heroin addiction.

An additional aim of the present invention discloses the synthesis and the molecular structure of a therapeutic anti-morphine/heroin vaccine formulation, validated in pre-clinic studies in the rodent, where this vaccine formulation containing the tetanus toxoid used as the immunogenic carrier protein to covalently haptenized morphine, provides its potential use to evaluate its therapeutical effects in clinical phases studies, by confering a long-term immunoprotection, maintenance of prolonged abstinence and relapse prevention in detoxified subjects from either morphine or heroin addiction.

A final aim of the present invention discloses the general methodology used to design, develop, apply and validate an efficient and atoxic therapy, whose mechanism of action differed from the available current classical therapeutic compounds, by enhancing pharmacokinetic changes of the aforementioned opiate drugs, thereby reducing efficiently their blood-brain barrier permeation, once they have been administered to a hyperimmune subjects, previously vaccinated against these two opiate drugs of abuse.

Collectively, the present invention discloses and provides a full description of the methodology and processes required to prepare intermediate derivatives for the synthesis of a morphine/heroin vaccine, pharmaceutical compositions or therapeutic formulations, including methods and therapeutical uses against morphine-heroin addiction.

BRIEF DESCRIPTION OF THE FIGURES

Other features and advantages of the present invention will be evident from the specific aims and preferred modalities described in the claims disclosed and footnotes accompanying drawings or figures, wherein:

DETAILED DESCRIPTION OF THE INVENTION

Figure 1:
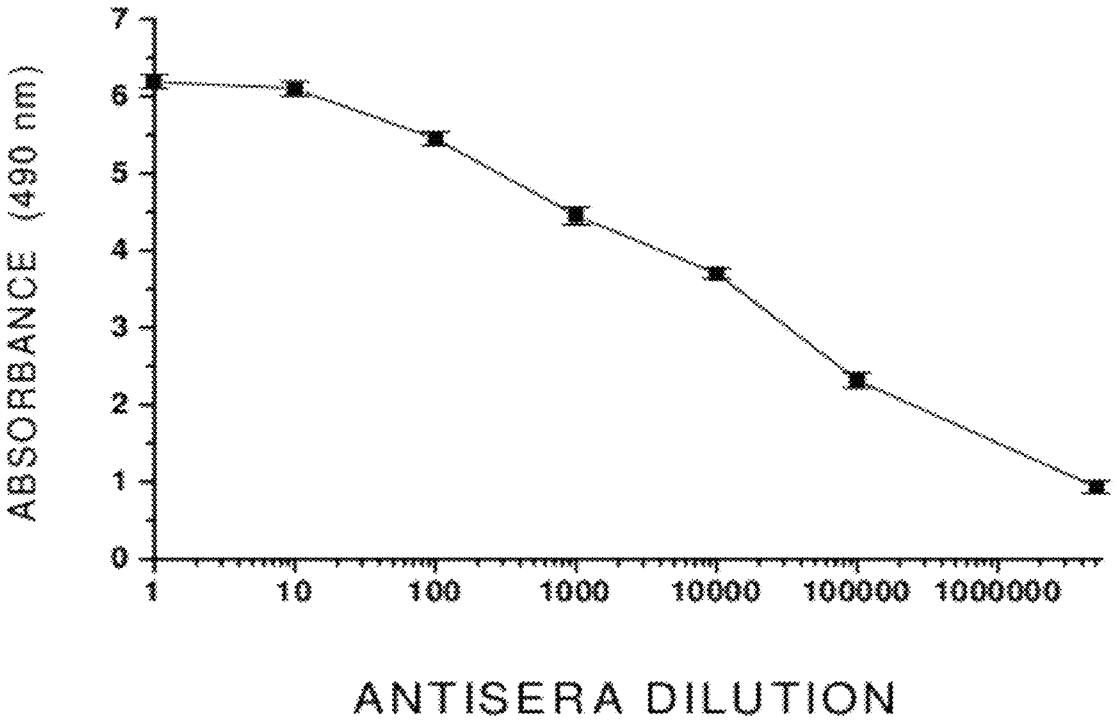
FIG. 1, depicts a representative immunoenzymatic antibody capture ELISA assay showing the robust humoral immune response induced by the novel tetanus toxoid-morphine immunogen characterized by high serum antibody titers generated against this opiate drug.

The scientific literature referred to in this section describes in full details the available information to skilled persons in this field. The present invention discloses and provides a therapeutical treatment for morphine and heroin addiction. This therapy is based on the pharmacological principle which describes the active vaccination with a novel structural formulation of a carrier protein-haptenic drug conjugate against these two opiates in subjects previously addicted and subsequently detoxified. The chemical composition of the therapeutic conjugate of the present invention consists of morphine as haptenic drug and the tetanus toxoid as the highly immunogenic carrier protein, being this latter carrier protein a highly immunogenic licensed protein used in human vaccination protocols. This highly immunogenic morphine-conjugate is able to stimulate the generation of high and sustained serum antibody titers against haptenized morphine when detoxified individuals against opiate addiction receive this therapeutic formulation. Thus, the use and application of adequate active immunization protocols, triggers the synthesis and enhances the generation of high serum anti-morphine antibody titers that recognize and bind with high specificity and avidity to the "free" unbound fraction of drug in plasma, after a subsequent re-exposure of the drug. This process eventually leads to a significant neutralization and/or prevention of the blood-brain barrier permeation of the opiate drug, thereby decreasing or preventing significantly the reinforcing properties of opiates in the brain. Thus, morphine and/or heroin are neutralized before reaching the brain tissue, and thereby, the detoxified addicted subject is not rewarded by the reinforcing pharmacological properties of these two drugs, which ultimately represent the underlying “pharmacological driving system” by which these two opiates enhance their reinforcing drug activities in the brain rewarding pathways. The active immunization paradigm inducing the neutralizing activity of these opiates occurs over a long-term period (i.e., 3-6 months) in vaccinated subjects treated with the bivalent vaccine against morphine-heroin addiction of the present invention. This is mostly due to the long-time course activity of the humoral immune response neutralizing these opiate drugs in plasma, mediated throughout the specific serum antibodies raised against the haptenized drug. In this context, it is expected that the established long-term stability of the immune response, mediated through the generation of high anti-haptenic-drug antibody titers, induced by the therapeutic composition of the present invention, represents an efficient immunogenic mechanism to maintain prolonged abstinence and/or prevent relapse to morphine and heroin addiction in previously detoxified subjects. Furthermore, the therapeutical vaccination approach against morphine/heroin addiction of the present invention is compatible with other therapies currently used to maintain prolonged abstinence and/or relapse prevention to opiate addiction. In this context, a large number of pharmacological agents used for these therapeutical purposes, such as methadone, buprenorphine, naloxone, naltrexone, etc., comprise among many other listed pharmacological drugs, the most selected therapeutical compounds used in clinics, which can be used simultaneously with the vaccination therapy discloses in the present invention.

The aim of the aforementioned parameters and the following examples listed below are shown to illustrate the particular issues required to carry out and perform the present invention and it should not be considered as limiting factors of the protective pursuit of the same.

EXAMPLES

1. Schematic Representation of the Molecular Structure of the Chemical Commercial Formulation of Morphine Used as Hapten for the Preparation of the Bivalent Vaccine Against Morphine-Heroin Addiction The chemical commercial formulation (Sigma-Aldrich) of the pentahydrated morphine-sulfate salt (MW 758.8, $C_{34}H_{40}N_2O_{10}S$) was used as the starting compound for synthesis of morphine base (see below, paragraph (a), under the section describing “A REACTION PROCESS FOR THE PREPARATION OF INTERMEDIATE DERIVATIVES USED FOR THE SYNTHESIS OF THE BIVALENT VACCINE AGAINST MORPHINE-HEROIN ADDICTION”) and then for the synthesis of the intermediate derivative morphine-6-hemisuccinate. This latter intermediate derivative was subsequently haptenized to the free epsilon amino groups from the lateral chain of exposed lysine residues in the tetanus toxoid through the sequential covalent cross-linking with the homo- and hetero-bifunctional cross-linking reagents, EDC and TFCS, respectively.

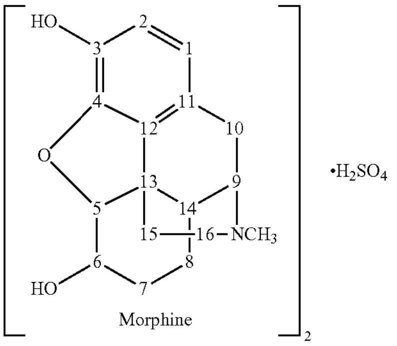

Morphine

2. Schematic Representation of the Structural Formulation of the 3-O-Carboxy-Methyl-Morphine Intermediate Derivative This intermediate derivative of morphine has been synthesized and used by several groups of researchers and it was also used in the present invention for the covalent haptenization of morphine to the tetanus toxoid, as an alternative bivalent vaccine against morphine-heroin addiction;

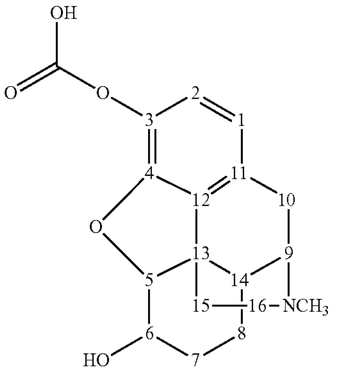

3-O-Carboxyl-methyl-morphine

3. Schematic Representation of the Structural Formulation of the Intermediate Derivative Morphine-6-Hemisuccinate This intermediate derivative of morphine has been synthesized and used by several groups of researchers and used in the present invention of the bivalent vaccine against morphine-heroin addiction for the covalent haptenization of this opiate substance to the tetanus toxoid;

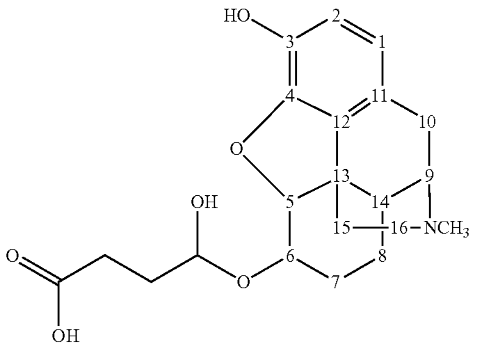

Morphine-6-Hemisuccinate

4. Schematic Representation of the Structural Formulation of the 3-O-Carboxy-Methyl-Morphine and Morphine-6-Hemisuccinate Intermediate Derivatives Covalently Condensed to the 1-Ethyl-3-(3-Dimethylaminopropyl)Carbodiimide (EDC)

The chemical reagent 1-ethyl-3-(3-dimethylaminopropyl) carbodiimide (EDC) has been used by several researchers in covalent haptenization reactions of the 3-O-carboxymethyl-morphine intermediate derivative to carrier proteins such as KLH and BSA. The EDC was also used for the covalent haptenization of the intermediate derivative morphine-6-hemisuccinate to the intermediate product complex tetanus toxoid-TFCS in the present invention of the bivalent vaccine against morphine-heroin addiction (see the reaction schemes of chemical synthesis in examples 5 (a-c) and 7 (a and b).

a)

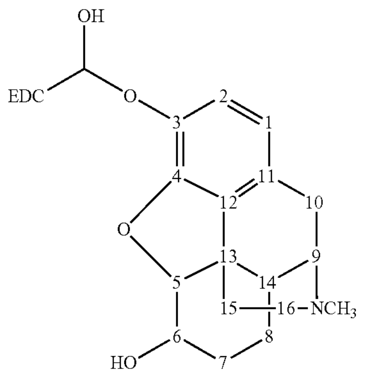

EDC-(3-O-Carboxymethylmorphine) intermediate derivative b)

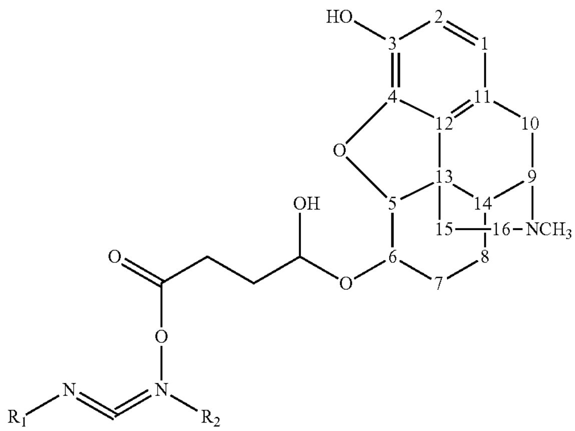

EDC-(Morphine-6-hemisuccinate) intermediate derivative

Synthesis of the Bivalent Vaccine Against Morphine-Heroin Addiction.

Figure 8A:
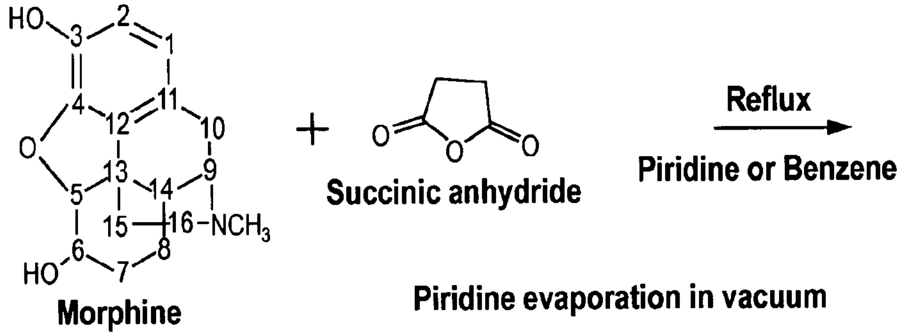
FIG. 8 depicts the preparation of the intermediate derivative of EDC-morphine-6-hemisuccinate.

The synthesis of the immunogenic conjugate of morphine in the present invention requires the initial chemical modification of the morphine molecule to generate a high reactive structural derivative of this opiate which provides free reactive carboxyl groups, used to covalent cross-link two hetero-bifunctional reagents used to form the chemical structure of the spacer linker arm which bind to the epsilon amino groups of the lateral chain of exposed lysine residues in the tetanus toxoid, the carrier protein used in the present invention (see example 6). The coupling chemistry procedures used to modify the structure and activate both 3 and 6 reactive hydroxyl groups of the phenantrenic ring of the morphine molecule in order to crosslink heterobifunctional reagents are very scarced (Robert T. Morrison and Robert N. Boyd, Organic Chemistry, 7th Ed., 2003), and only very few methods using this chemical synthesizing approaches have been reported. In this context, from the beginning of the 70s, different research groups (B. Wainer et al., Science 176: 1143-1145, 1972; B. Wainer et al., Science 178: 647. 1972; B. Wainer et al., J. Immunol. 110(3):667-673, 1973; Wainer et al., Nature, 241:537-538, 1973 and B. Hill et al., J. Immunol. 114:1363-1368, 1975); reported a non-patented, classical chemical-based methodology, found today in organic chemistry textbooks, which uses succinic anhydride as reagent to modify the reactive 6-hydroxyl group of the phenantrenic ring structure of the morphine molecule. This primary morphine intermediate, referred to as morphine-6-hemisuccinate (see example 3, and FIG. 8B) differs from morphine in its highly reactive free carboxylic acid of the succinyl-ester group (previously linked to the morphine molecule) which can be covalently linked (see FIG. 8A) to homobifunctional croos-linking reagents such as the 1-ethyl-3-(3-dimethylaminopropyl)-carbodiimide (EDC) (see example 3, and FIG. 8C). This reagent has been widely used in covalent crosslinking chemical reactions for the covalent condensation of free functional amino and carboxyl groups from donor molecules (S. Hockfield et al., Molecular Probes of the Nervous System: Selected Methods for Antibody and Nucleic Acid Probes, Vol. 1, Cold Spring Harbor Laboratory Press, New Cork, 1993).

As morphine is not an immunogenic molecule by itself, the generation of humoral immune responses with high titers of specific antibodies against molecules of relative low structural complexity as this opiate represents a serious methodological challenge. In the present invention, the structure of the morphine conjugate was initially designed and followed by the synthesis of morphine-6-hemisuccinate intermediate derivative (FIG. 8B) which in turn was covalently haptenized to lysine residues in the tetanus toxoid, used as carrier protein, via the sequential synthesis of a spacer-linker arm, structurally conformed by the chemical condensation of the 1-ethyl-3-(3-dimethylaminopropyl)carbodiimide (referred to as the commercial compound EDC, see example 5) and the N-(ϵ-trifluoracetylcaproyloxy)-succinimide-ester (referred to as the commercial compound TFCS, see example 6). This procedure, based on the covalent condensation of haptenized morphine to tetanus toxoid via this long spacer linker arm, formed by the covalent condensation of EDC and TFCS reagents, allows the structural preservation of the morphine molecule once haptenized with the tetanus toxoid. In this structural context, it is expected that the morphine remains fixed to the carrier protein in such a way that it could keeps its original steric configuration. This, in principle, could facilitate that other free domains and/or reactive groups within the morphine molecule, other than the active domains of the opiate drug contributing to the covalent haptenization with the carrier protein, it could be exposed and contribute as the predominant antigenic domains or antigenic determinants in the native drug molecule recognized by the humoral immune response. Additionally, the chemical nature of the hydrocarbonated structure of the spacer-linker arm (see example 6) confers to this carbon backbone a complete inert structure to any chemical reactivity, and thereby, a very low immunogenicity per se. These structural and functional properties conferred by the hydrocarbonated linker arm contributes could contribute to the immunopredominant epitogenic role of morphine in the structural formulation of the present invention of the bivalent vaccine againts morphine-heroin addiction. Thus, the above proposed capabilities, structural and functional advantages of the present invention are supported by the experimental results showing its high efficacy to produce a strong humoral immune response (see FIGS. 1 and 2), with high and sustained specific serum antibody titers (see FIGS. 3 and 4) that cross-recognize with equivalent specificity non-haptenized morphine, including the structural opiate analogues, heroin and the endogenous opiate metabolites, such as the 6-monoacetylmorphine and their active (addictive) glucuronide by-products (i.e. morphine-3-6-glucuronides) (see FIG. 5). The most plausible explanation for the specificity of this humoral immune response triggered by our novel vaccine model against these opiate compounds is based on the antigenic presentation of different structural domains of morphine to the immune system. This appears to be due to the structural length of the spacer linker arm that separate morphine from the tetanus toxoid in such a way that allows the immune system to react against to specific antigenic determinants of the phenantrenic structure of morphine shared by other structural opiate analogues and its endogenous metabolites as well (i.e., heroin and morphine-3-6-glucuronides).

5. Procedures and Reactions Used for the Preparation of the Intermediate Derivative of Morphine Required for the Synthesis of the Bivalent Vaccine Against Morphine-Heroin Addiction a) Initial Preparation of Morphine Base from the Pentahydrated Morphine Sulfate Salt (a Commercially Available Chemical Formulation of Morphine).

Morphine base (FIG. 8A) was synthesized from the commercial sulfate salt of this opiate substance (Sigma-Aldrich), according to a classical chemical procedure reported in 1972 by E. J. Simon (E. J. Simon et al., Proc. Natl. Acad. Sci. USA, 69: 1835-1837, 1972). This reaction was carried out as follows; 64 mg of morphine sulfate/ml were dissolved in distilled water at room temperature under constant stirring. The pH of this solution was adjusted at 8.0 with $NH_4OH$. The morphine base was subsequently crystallized through precipitation at pH 8, filtered and dried through evaporation at 60° C. under vacuum conditions.

b) Preparation of the Intermediate Derivative Morphine-6-Hemisuccinate (M-6-H).

Figure 8B:
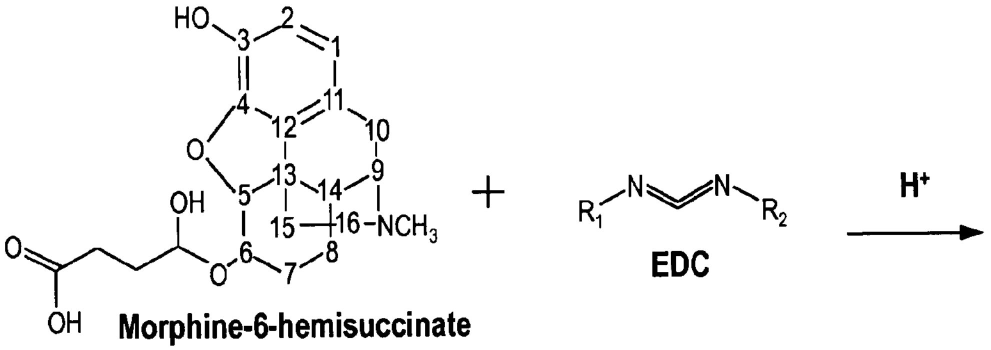
Figure 8C:
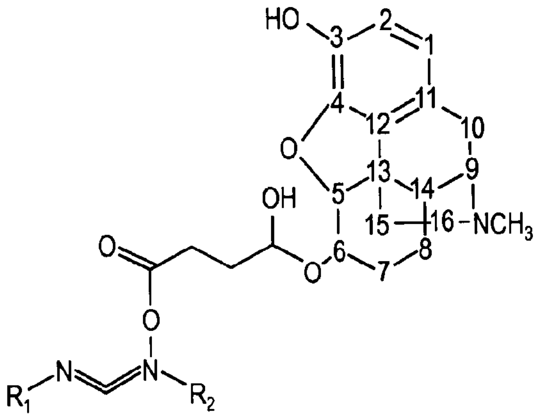

The M-6-H compound was prepared from morphine base, according to the following protocol and subject to modifications from standard pioneer procedures reported in the 70s by B. Wainer et al., Science, 176-1143-1145, 1972; B. H. Wainer et al., Science, 178:647, 1972, B. Wainer et al., J. Immunol. 110 (3):667-673, 1973; Wainer et al., Nature, 241:537-538, 1973 and B. Hill et al., J. Immunol. 114:1363-1368, 1975. The chemical reaction procedure was performed as follows; for each gram of morphine-based, 2 grams of succinic anhydride (Sigma-Aldrich) was added to the reacting mixture, followed by incubation with 20 ml of pyridine or dry benzene under continous reflux in a glass flask. After warming the reacting mixture for up to 6 hours at reflux temperature (70-80° C.), the reaction mixture was slowly cooled at room temperature and the excess of pyridine or benzene was decanted. The rest of these latter organic components were evaporated using a continous nitrogen stream under reduced pressure, producing a dry product residue represented by M-6-H. This product was exposed to 10 times-washed out periods with 60% ethanol in distilled water to achieve recrystallization of the M-6-H residue (FIG. 8B). The percentage yield of the product was quantified by a standard analytical method, using thin layer chromatography analysis (TLC, the initials of the abbreviated conventional nomenclature of this procedure) (B. Wainer et al., Science 176:1143-1145, 1972). This method was approached as follows; 100 μg of the synthetic M-6-H residue and an equivalent amount of morphine base (compound used as reference control) were dissolved in the solvent system of ethyl acetate:methanol:ammonium hydroxide (85:10:5, v:v:v), followed by sampling 1 μl/lane, dried at room temperature and runned in the silica thin layer chromatography matrix with the aforementioned solvent system. After the compounds have been chromatographically runned, the silica thin layer is exposed to UV lamp stimulation at 285 nm, (this wavelength is normally used to excite the chromophore represented by the phenolic ring of the phenantrenic structure in the free morphine and M-6-H, respectively). In this context, the TLC profile of the synthetic M-6-H residue exhibited a relative mobility coefficient (Rf, its conventional abbreviated initials in English [Retention factor]) of about 0.1-0.15, whereas the morphine-free-based exhibited a larger Rf of about 0.3-0.4. The average yield of the M-6-H product in a standard synthetic reaction was always approximately 95% or more.

c) Preparation of the Intermediate Derivative of EDC-Morphine-6-Hemisuccinate.

To achieve the covalent haptenization of M-6-H with the carrier protein, the intermediate derivative M-6-H was covalently conjugated through its the succinyl-free carboxyl group to the homobifunctional covalent crosslinker reagent, EDC (1-ethyl-3-(3-dimethylaminopropyl)carbodiimide (Pierce) (see FIG. 8C), according to the standard protocol described by the manufacturer (Pierce). During this condensing reaction, the excess of EDC that did not react with the succinyl-carboxylic group is rapidly hydrolyzed to a non-reactive intermediate derivative compound, due to the high unstability of this reagent when placed in an aqueous solution. Thus, a standard coupling reaction consisted in mixing 100 mg of EDC to each 100 mg of M-6-H dissolved in 100 ml of distilled $H_2O$, at pH 5.5, adjusted with a 1N HCl solution. The reaction mixture is then incubated at 37° C. for 2 hours under constant stirring. Under these conditions, a yield of approximately 98% of EDC-(M-6-H) product is regularly obtained under these coupling conditions. This estimation was obtained by the titrating the free carboxylic groups of equivalent samples of both the M-6-H product, used as control, and the EDC-(M-6-H) product with 1N NaOH solution, a standard biochemical procedure normally used to verify the presence of free carboxylic groups at pK values of around 4.2. This reaction procedure generates optimum yields of synthetic EDC-(M-6-H) product, which is usually unstable in aqueous solutions and thereby, requires to be reacted rapidly with amino groups from the tetanus toxoid-TFCS intermediate derivative, whose synthesis is disclosed in the present invention of the bivalent vaccine against morphine-heroin addiction, and serves as the carrier protein of same invention.

a)

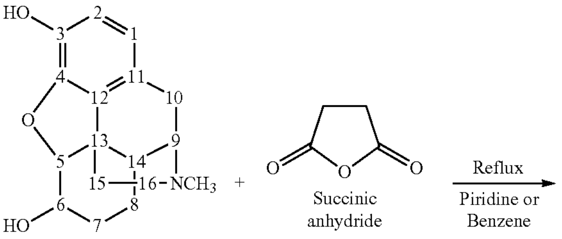

Morphine

Succinic anhydride

Piridine evaporation in vacuum b)

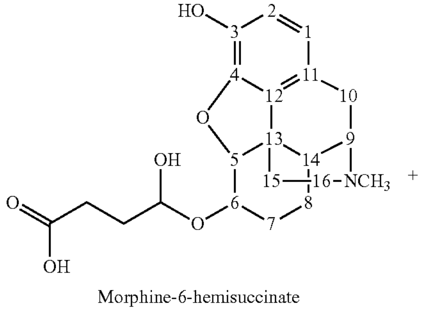

Morphine-6-hemisuccinate

-continued c)

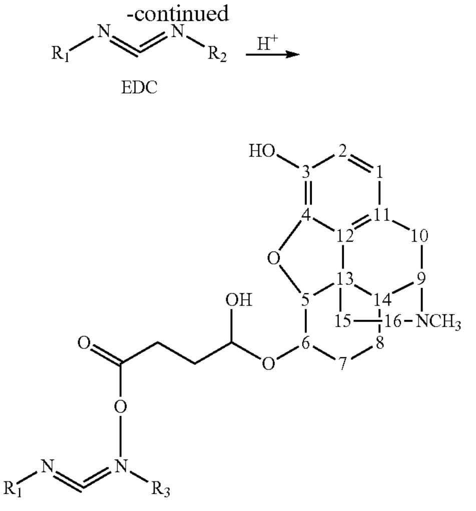

EDC-(Morphine-6-hemisuccinate) intermediate derivative

6. Reaction Process Used for Preparation of the Tetanus Toxoid-Intermediate Derivative Used as Carrier Protein (CP) Covalently Condensed with the N-(ϵ-Trifluoroacetylcaproyloxy)-Succinimide Ester (TFCS): CP-TFCS Complex.

Figure 9A:
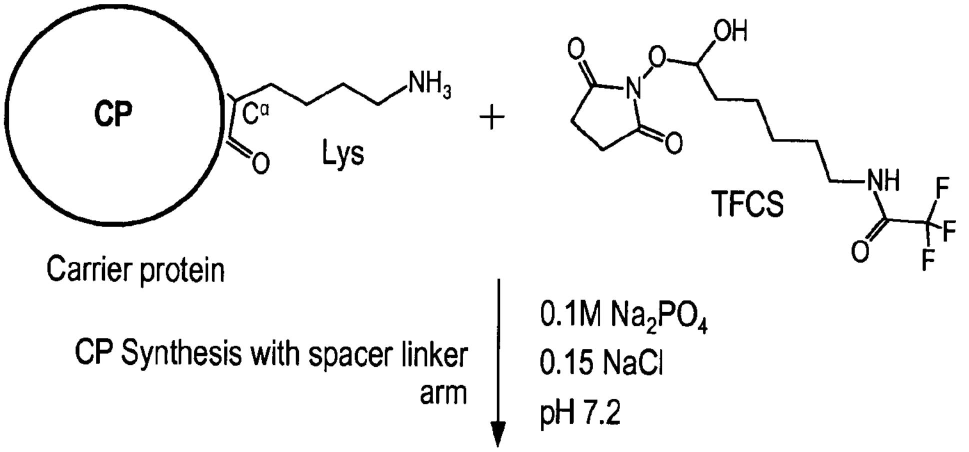
FIG. 9 depicts the reaction process used for preparation of the tetanus toxoid-intermediate derivative used as carrier protein (CP) covalently condensed with the N-(ϵ-trifluoroacetylcaproyloxy)-succinimide ester (TFCS): CP-TFCS complex.
Figure 9B:
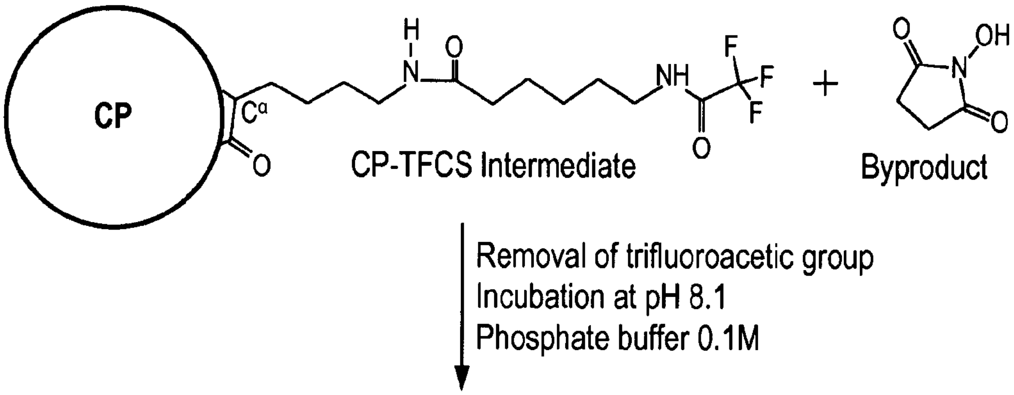
Figure 9C:
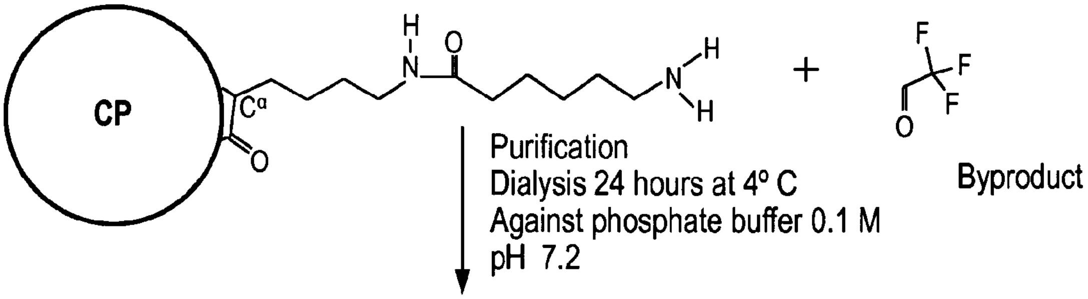

The tetanus toxoid preparation used as carrier protein (CP) in the present invention of the bivalent vaccine against morphine-heroin addiction, had certified degree of purity (≧98%) and a total lack of toxicity. This protein preparation is formed by the H-polypeptide subunit, which contains approximately 858 amino acid residues, with molecular mass of about 100 kDa. This protein subunit obtained through standard DNA recombination techniques, is encoded by the *Clostridium tetani* gene, which produces the native bacterial tetanus toxin, and contains only 68 copies of lysine residues along its primary amino acid sequence of the H-polypeptide toxoid protein, whereas the native tetanus toxin consists of 1313 amino acid protein, rendering its high molecular mass of 150,700 daltons (150.7 kD. In order to acieve the synthesis of the tetanus toxoid-TFCS reactive intermediate, the ϵ-amino sites of exposed lysine residues in this protein are covalently conjugated to the N-(ϵ-trifluoroacetylcaproyloxy)-succinimide ester (TFCS, Pierce) (see FIGS. 9A-9C). The TFCS is a heterobifunctional covalent cross-linker reagent used to conjugate, at pH 7-7.5, free ϵ-amino groups in the lateral chain of exposed lysine residues from high molecular mass proteins, via its N-hydroxysuccinimide-ester active site. Thus, this reaction enhances the synthesis of the tetanus toxoid-TFCS intermediate derivative through the formation of stable amide bonds. The reaction procedure used to synthesize the tetanus toxoid-TFCS conjugate as an intermediate step required for the synthesis of the present invention of the bivalent vaccine against morphine-heroin addiction is described in FIG. 9B. The coupling procedures and experimental conditions used to carry out a typical synthesis of this protein carrier-TFCS complex consisted in the initial preparation of 40 mg/ml of a TFCS-stock solution (134 mM) (prepared in fresh and always immediately before use) dissolved in a solution containing 10-20% DMSO/90-80% deionized $H_2O$ (v:v). The TFCS reagent is immediately mixed with the tetanus toxoid protein, in a molar excess ratio of TFCS 10-20 fold with respect to the toxoid itself. Thus, for example, a typical reaction consists in the mixture of 100 mg (0.5 mM) of tetanus toxoid dissolved in 4 ml of a solution containing phosphate-buffered saline solution (PBS=0.1 M of PB/0.15 mM NaCl, pH 7.2) with 50 μl of the TFCS stock solution (the final concentration of TFCS and DMSO achieved in the mixture of tetanus toxoid-TFCS solution is 6.7 mM and 0.5-1%, respectively). Noteworthy, is the fact that the initial concentration of DMSO during the covalent condensing reaction between the carrier protein and the TFCS reagent should reach a final 1:10-20 dilution (v:v), in order to prevent the formation of protein precipitates in the mixture. The condensation reaction occurring between the tetanus toxoid and TFCS should take place at room temperature for 60-90 minutes, in order to achieve the complete synthesis of the tetanus toxoid-TFCS product. This intermediate derivative product still preserves a reactive amino group protected chemically by a trifluoroacetyl group (see FIG. 9B), which is subsequently hydrolyzed after exposing the product to an additional 2-3 hour incubation period at room temperature in a PBS solution, pH 8-8.5. The pH of this latter phosphate-buffered solution should be adjusted with a solution of 10 N NaOH. Under these experimental conditions, the free reactive amino groups in the conjugated TFCS compound are generated at the deprotected end site of the tetanus toxoid-TFCS complex (see FIG. 9B). This final tetanus toxoid-TFCS intermediate derivative product is subsequently exposed to purification procedures using standard dialysis protocols. Briefly this method consists in incubating the tetanus toxoid-TFCS conjugate, placed inside a 10 kDa cut-off dialysis membrane (Sigma-Aldrich)] against three changes of 6 liters of 0.1 M phosphate buffer solution, pH 7.2, at 4° C. every 8 hours during a 24 hour period.

a)

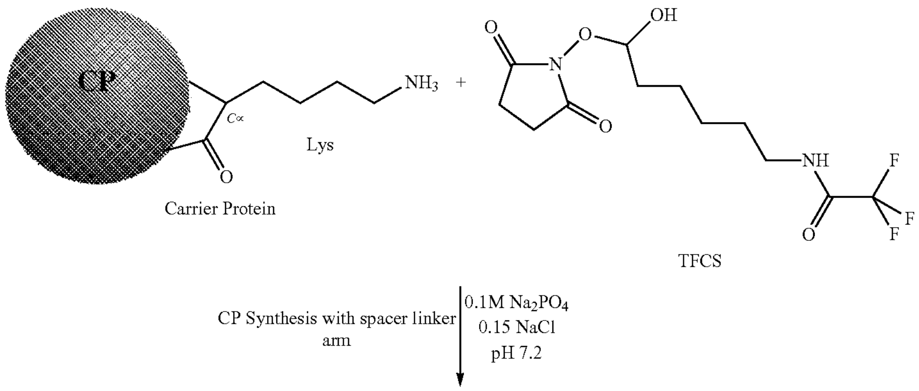

-continued

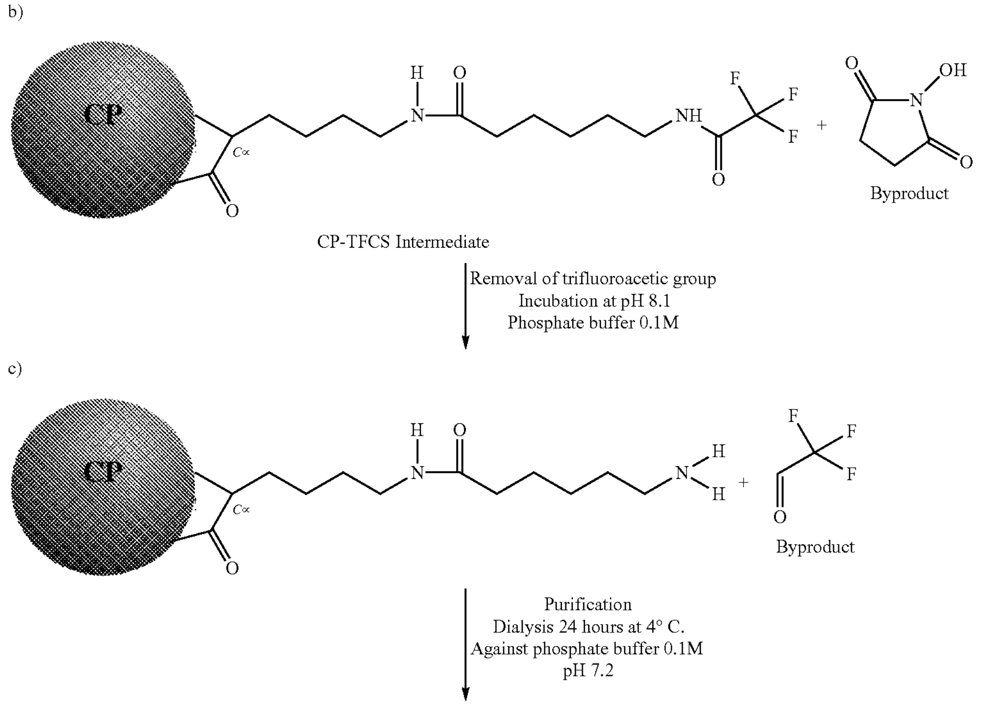

Figure 10A:
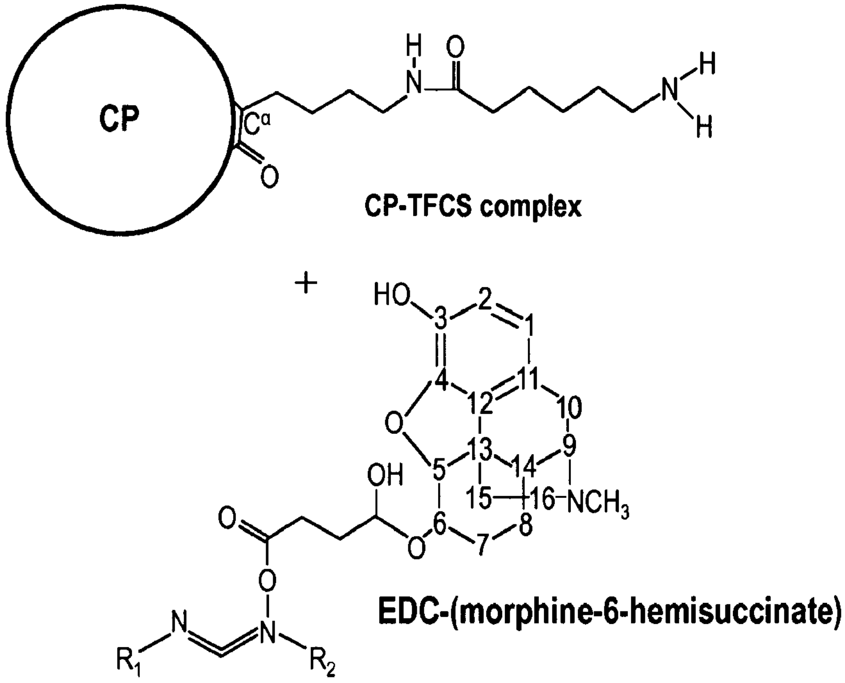
FIG. 10 depicts covalent condensation of the intermediate product of morphine, the EDC-(M-6-H) to the tetanus toxoid-TFCS complex.
Figure 10B:
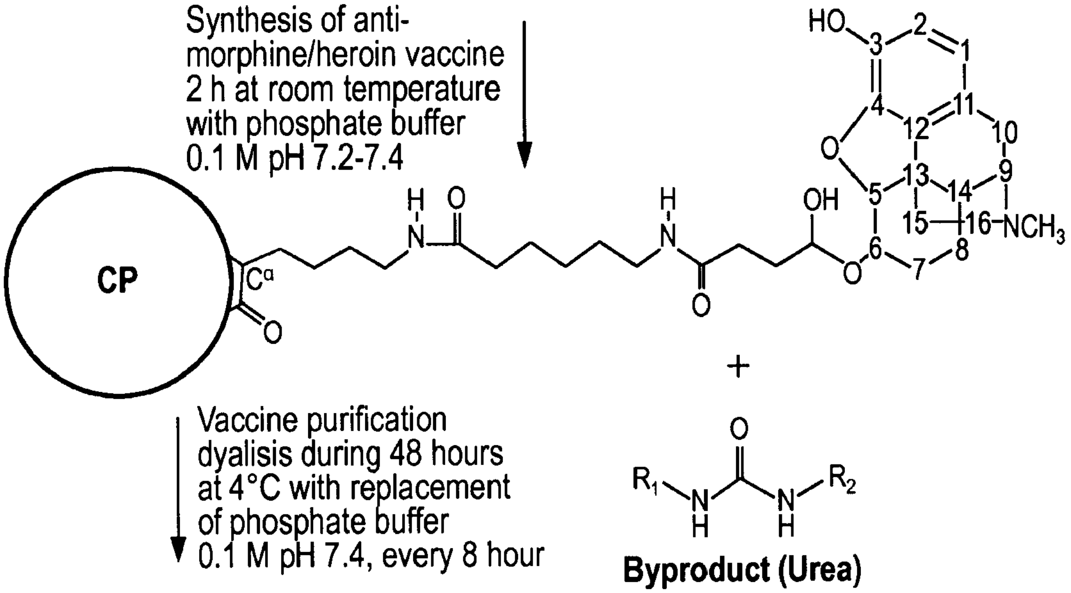

7. Tetanus Toxoid-TFCS Intermediate Derivatives: Synthesis of the Final Structural Formulation of the Bivalent Vaccine Against Morphine-Heroin Addiction The covalent condensation of the intermediate product of morphine, the EDC-(M-6-H) to the tetanus toxoid-TFCS complex (see FIG. 10A) is achieved through a stable amide covalent bond, formed after the reaction between the free carboxyl groups exposed at the end of the EDC-(M-6-H) conjugate and the unprotected free amino groups from the TFCS reagent linked to the tetanus toxoid (the TFCS-tetanus toxoid molecular complex, see FIG. 10B).

Due to that the complete synthesis and purification procedures of the tetanus toxoid-TFCS derivative requires at most a 24 hour period, the synthesis of the EDC-(M-6-H) conjugate should be carried out just after the completion of the reaction-purification steps of the tetanus toxoid-TFCS conjugate. This is mostly due to the fact that the EDC-(M-6-H) product is very unstable and easily to hydrolyze when exposed to prolong storage (i.e., more than two hours) even at temperatures below 10° C. Other important issues that require considerable attention for the optimization of the covalent condensation between the EDC-(M-6-H)-conjugate and the tetanus toxoid-TFCS product, are referred to the concentration of the reactants added in the chemical reaction. The tetanus toxoid used as the carrier protein, exhibits a molecular weight of about 100 kDa, containing an approximate number of 68 lysine residues. The exposed ε-amino groups (active sites) in the lateral chain of these amino acid residues, allow the covalent condensation of TFCS during the synthesis of the present invention of bivalent vaccine against morphine-heroin. In this context, each μmol of tetanus toxoid (100 mg) contain an apprimated density of up to 0.07 μmol of available active sites (unprotected free amino groups) that could be covalently linked with the TFCS reagent. Furthermore, our condensation reaction between the EDC-(M-6-H) intermediate derivative and the tetanus toxoid-TFCS conjugate uses a stoichiometric mol:mol ratio of 100 μmol of the EDC-(M-6-H) for each 0.07 μmol of amino groups of the tetanus toxoid-TFCS conjugate.

In a typical formulation of the covalent condensation between the EDC-(M-6-H) intermediate derivative and the tetanus toxoid-TFCS conjugate, the concentration of reagents and the reaction conditions require the mixture of 100 mg of tetanus toxoid-TFCS complex (1 μmol tetanus toxoid-TFCS=0.07 μmol of free amino groups/active sites) plus 30 mg of the EDC-(M-6-H) intermediate derivative (70 μmol of active sites for covalent condensation), dissolved in 100 ml of 0.1 M phosphate/0.15 M NaCl buffer solution, adjusting the pH to 7-7.5 (being the calculated molecular mass of the latter EDC-(M-6-H) compound of up to 426.37 daltons). The reacting mixture is incubated at room temperature during 2-3 hours under constant stirring. The synthetic product obtained, the morphine-6-hemisuccinyl-tetanus toxoid vaccine, is then purified using standard dialysis procedures using 10 kDa cut-off dialysis membranes (Sigma-Aldrich) against six changes of 6 liters of 0.1 M phosphate buffer solution, pH 7.2, at 4° C., over a 48 hour period, in order eliminate the by-products formed during the reaction, such as urea and the non-haptenized EDC-(M-6-H) intermediate derivative.

Once the purification of the morphine-6-hemisuccinyl-tetanus toxoid vaccine has been completed, the dialyzated solution is subsequently sterilized by filtration in 0.45 μm pore size membrane filters (Gelman Sci) under positive pressure. Finally, 1 ml aliquots of the filtered solution are dry-frozen, lyophilized in sterile glass vials, sealed under vacuum and preserved under storage at 4° C. Several agents used normally to stabilize and prevent degradation of conjugates during dry-freezing and storage procedures (E. Harlow and D. Lane, Antibodies; A Laboratory Manual, Cold Spring Harbor Laboratory, New York, (1988) can be added to the therapeutic formulation of the present invention of the bivalent vaccine against morphine-heroin addiction. Examples of selected agents, consist of jelly, peptone, dextrine, methylcellulose, sucrose, lactose, maltose, glucose, fructose, sorbitol, glycerol, manitol, inositol, citric acid, tartaric acid, polyethylenglycol, and polyvinylpirrolidone, among many others. Each vial of the bivalent vaccine product against morphine-heroin addiction contains an average dose of about 1 mg of dry-frozen product of tetanus toxoid used as "reference dose unit". The protein concentration of each dose unit of the bivalent vaccine was determined by a standard protein quantification method using a bicinchoninic acid reaction kit, according to the procedures recommended by the manufacturer (Pierce Chemical). The quantitative measurement of percentage of incorporation of the EDC-(M-6-H) intermediate derivative covalently condensed to the free amino groups of the tetanus toxoid-TFCS complex was carried out by standard titration procedures, using the o-phtaldehyde reagent for titering the number of free amino groups of the tetanus toxoid-TFCS intermediate derivative (J. Cashman et al, J. Pharmacol. Exper. Ther. 293: 952-961, 2000). Percentage yield of up to 75-85% of hapten conjugation (morphine) with the carrier protein (tetanus toxoid) are normally achieved in the present formulation of the bivalent vaccine against morphine-heroin addiction.

The carrier protein used in this bivalent vaccine can be selected among many other proteins such as ovalbumin, rabbit serum albumin, thyroglobulin, fibrinogen, KLH, goat erythrocyte membranes and flagellin as well as toxoids from diphtheria, cholera and botulinic toxins, which may be covalently linked to the M-6-H intermediate derivative, using the synthetic conjugation procedure with the EDC and TFCS described above. The final product obtained may be used then, in active immunization experiments against morphine-heroin and/or used as solid-phase adsorbed antigens in immunological assays (i.e., ELISAs).

In the present invention, a morphine-6-hemosuccinyl-BSA conjugate was synthesized in parallel to the present invention of the bivalent vaccine against morphine-heroin addiction using similar synthetic protocols for this latter vaccine. The rationale to synthetize this additional morphine conjugate, was for using it as a morphine antigen adsorbed to the solid phase of our antibody-capture ELISA immunoenzymatic assays. These latter assays were used to identify, monitor, quantify (FIGS. 1-4) and validate the specificity (FIG. 5) of the humoral immune response induced by active vaccination with the therapeutic formulation of the present bivalent vaccine against morphine-heroin addiction.

a)

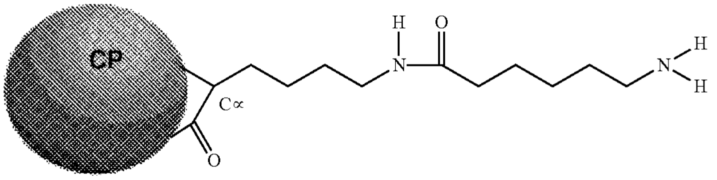

CP-TFCS complex

+

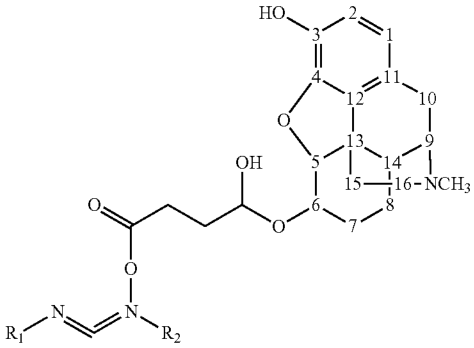

EDC-(morphine-6-hemisuccinate)

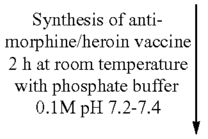

-continued b)

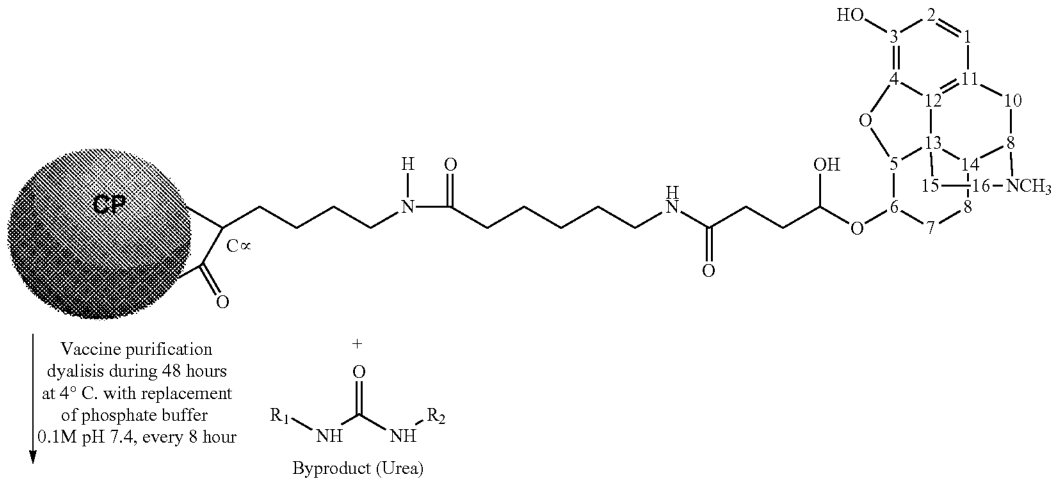

Byproduct (Urea)

8. Molecular Structure of the Bivalent Vaccine Against Morphine-Heroin Addiction The structural formulation of the present invent of the bivalent vaccine against morphine-heroin addiction shows for the first time the use of the chemical reagent, TFCS, used for the synthesis of a long spacer-linker arm to haptenize morphine and/or heroin to the tetanus toxoid.

Figure 4:
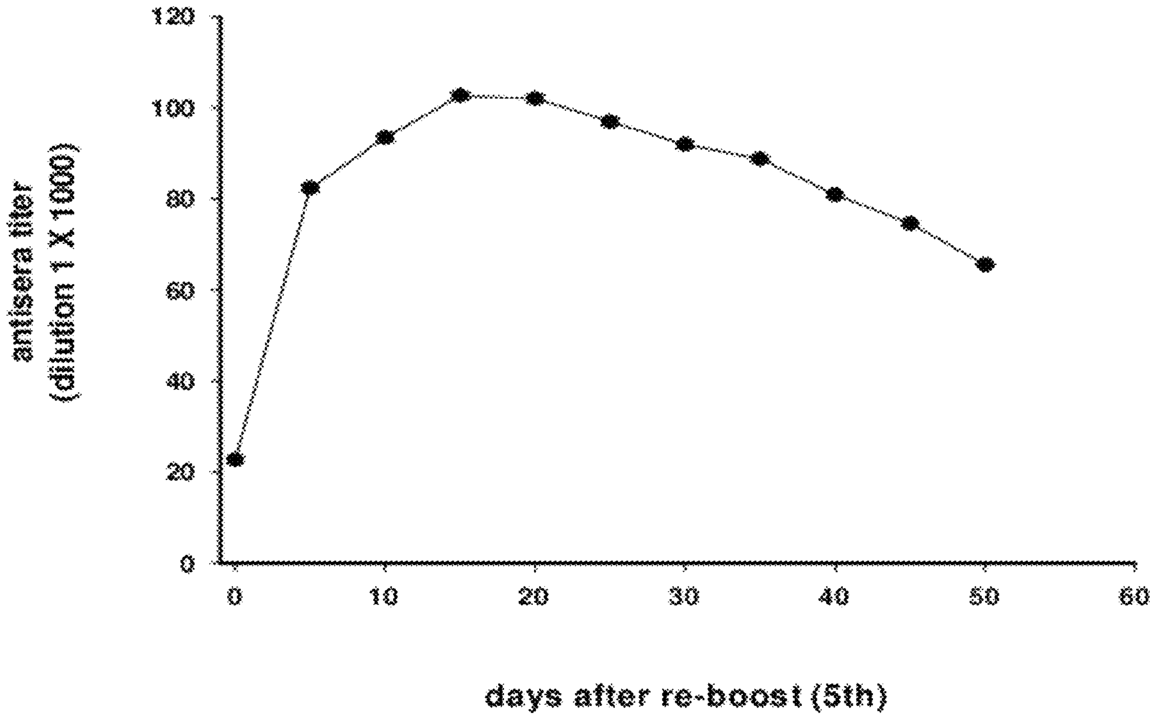
FIG. 4, depicts a representative plot of antibody capture immunoenzymatic ELISA assays used to monitor the recovery of the morphine/heroin specific antibody titers induced after a subsequent fifth boost with the new tetanus toxoid-morphine immunogen.
Figure 5:
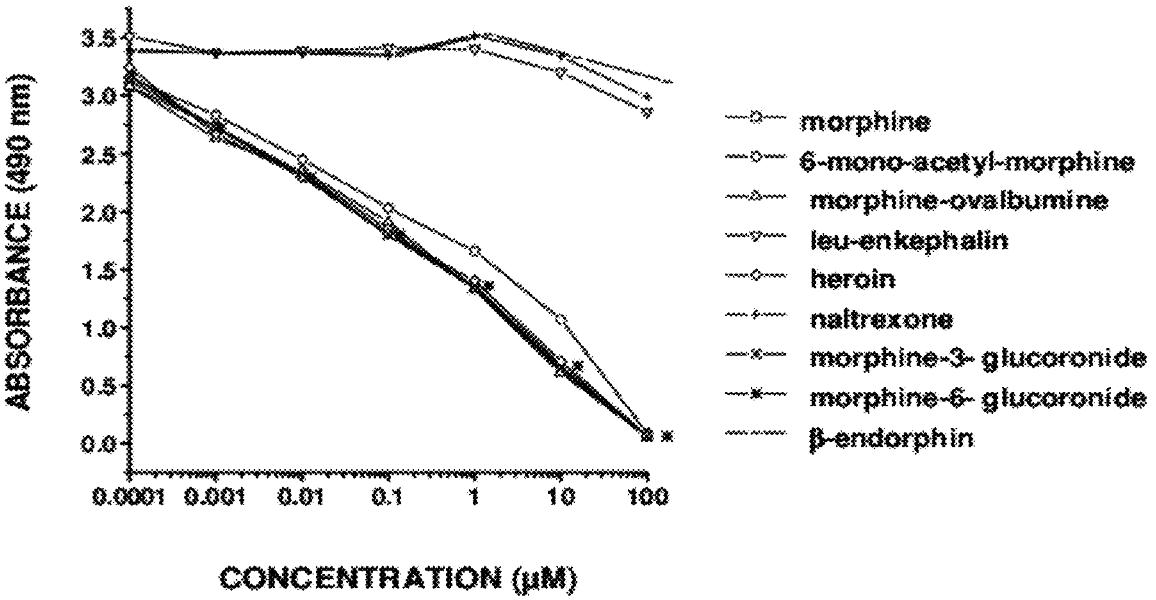
FIG. 5, depicts a competitive immunoenzymatic ELISA assay used to evaluate potential cross-recognition of the anti-morphine/heroin serum antibodies for different structurally-related analogues to morphine and heroin, used in classical anti-addictive therapy against these two opiate compounds, including the biotransformation metabolites from these two drugs, as well as different endogenous opioid neuropeptides involved in the regulation of different physiological and neural bioactivities in the CNS of mammals.
Figure 6:
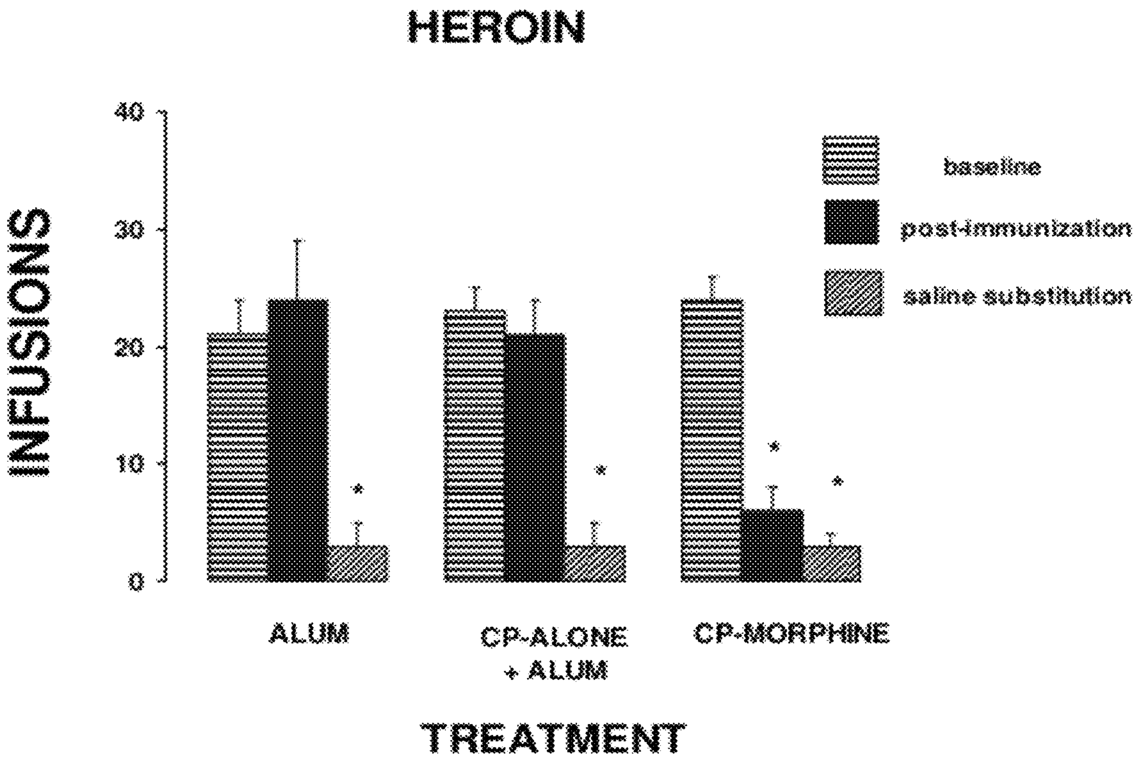
FIG. 6, shows the immunoprotective effect induced by the active vaccination with the tetanus toxoid-morphine immunogen in the rat, for blunting the intravenous self-administration behavior to heroin in the same animal and finally.
Figure 7:
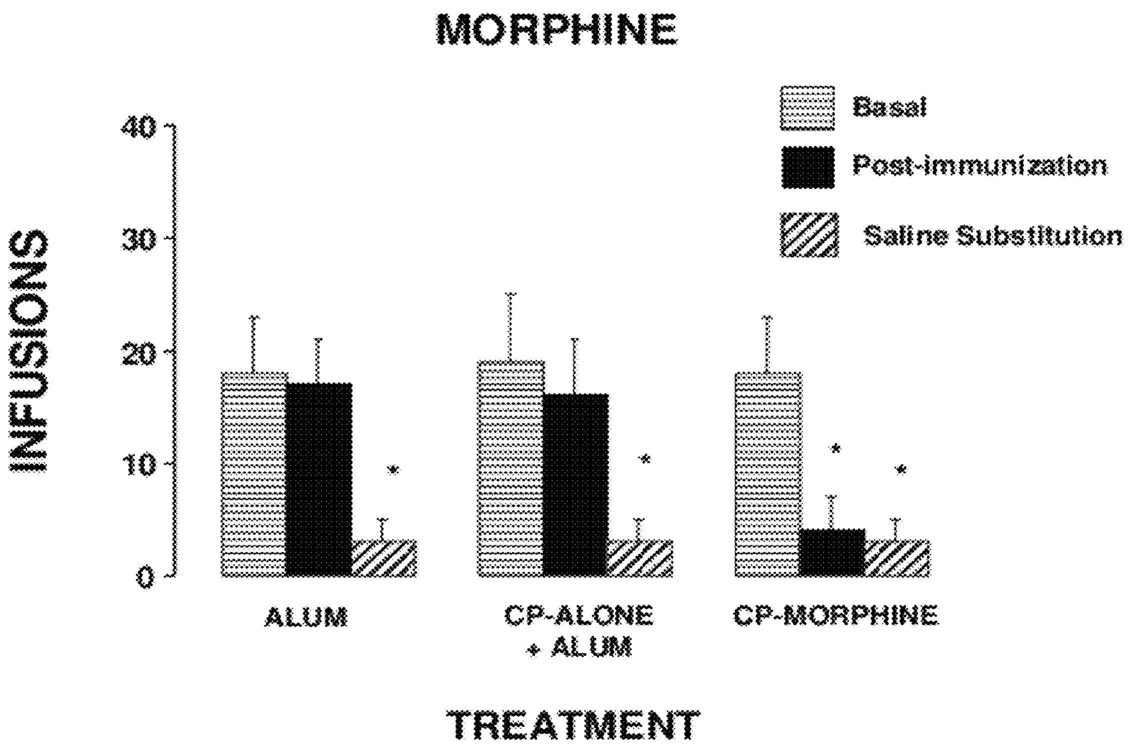
FIG. 7, shows the immunoprotective effect induced by active vaccination with the tetanus toxoid-morphine immunogen in the rat for blunting the intravenous self-administration behavior to morphine in the same animal.

A total molecular size of up 20.15 Å is calculated for the spacer-linker arm that separates the haptenized morphine covalently linked through the 6-carbon atom in its phenantrenic ring structure. The size of this spacer linker arm is significantly longer (see FIG. 11) from those used to synthesize previous reported morphine immunogens. This latter immunogens used the EDC reagent as homobifunctional cross-linker to covalently link the 3-O-carboxymethylmorphine and/or M-6-H to the ε-amino groups of exposed lysine residues in either BSA or KLH molecules, used as carrier proteins. For instance, the immunogenic conjugate of morphine-6-hemisuccinyl-BSA or morphine-6-hemisuccinyl-KLH contain a spacer-linker arm size of about 12.4 Å, because they lack the 6 carbon atom extension produced by the hydrocarbonated chain of the TFCS reagent. The addition of this hydrocarbonated chain from the TFCS in our vaccine formulation increases the length of the total spacer linker arm by about 7.74 Å, (see FIG. 11). As mentioned above, this structural innovation of the increased length of the spacer-linker arm in our novel model of anti-morphine-heroin vaccine model disclosed in the present invention shows important functional capabilities. These are demonstrated by the following experimental findings: a) high immunogenicity generated against haptenized morphine and/or heroin; and b) a superior capacity to triggers a robust humoral immune response with high and sustained titers of specific serum anti-morphine antibodies (FIGS. 1-4) which display equivalent cross-recognition to this opiate and its structural analogue, heroin (FIG. 5). Moreover, it is feasible to hypothesize that the increased length of this new spacer-linker arm introduced in the structural formulation of our bivalent-vaccine model against morphine-heroin addiction, offers structural and functional advantages, based on the humoral immune response produced by this immunogen, where sera antibodies cross-recognize with equivalent specificity the immunogenic epitopes exposed by the haptenized morphine molecule to the immune system of vaccinated animals which are shared by heroin and their endogenous metabolites 3-monoacetyl-morphine and the 3- and 6-morphine-glucuronides (FIG. 5). Additionally, the active vaccination with our novel morphine-heroin bivalent immunogen, disclosed in the present invention, may be used as an effective therapeutic procedure to induce a robust humoral immune response able to immunoprotect against the acquisition of addictive behaviors to these two opiate compounds in the actively vaccinated host. Finally, this humoral immune response induced by active vaccination in the host, may offer an immunoprotection against the endogenous activity of the aforementioned endogenous metabolites of both morphine and heroin, shown to display reinforcing addictive properties in detoxified and abstinent subjects from their addiction to these opiate compounds (FIGS. 6 and 7).

Figure 11:
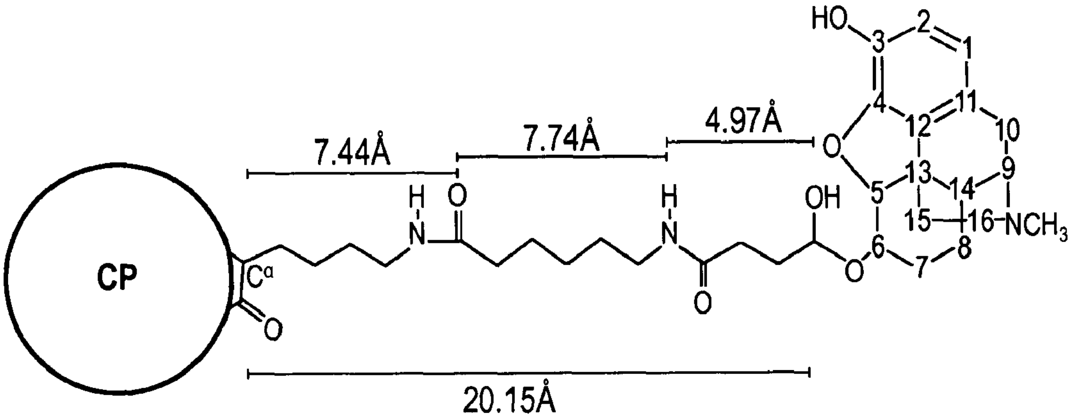
FIG. 11 depicts the molecular structure of the bivalent vaccine against morphine-heroin addiction.

In short, the spacer-linker arm exhibits a molecular size of 20.15 Å, where the 7.74 Å middle segment corresponds to the hydrocarbonated backbone introduced by the TFCS reagent, which has been covalently conjugated to the ε-amino groups of exposed lysine residues in the tetanus toxoid carrier protein; the 7.44 Å end-segment comprises the α-carbon atom and the next four carbon atoms of the lateral chain of lysine residues and the 4.97 Å condensed segment comprise the hemisuccinyl residue, which has been covalently linked via an ester group to the 6-carbon atom of the phenantrenic ring structure of the morphine molecule, as shown in FIG. 11.

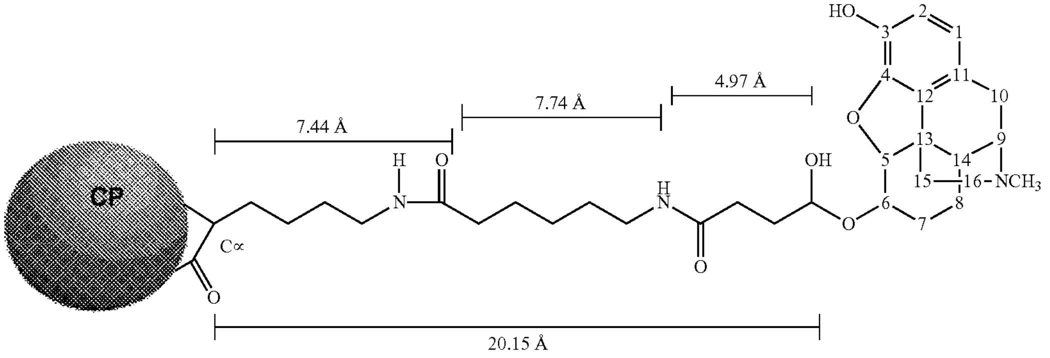

Figure 12A:
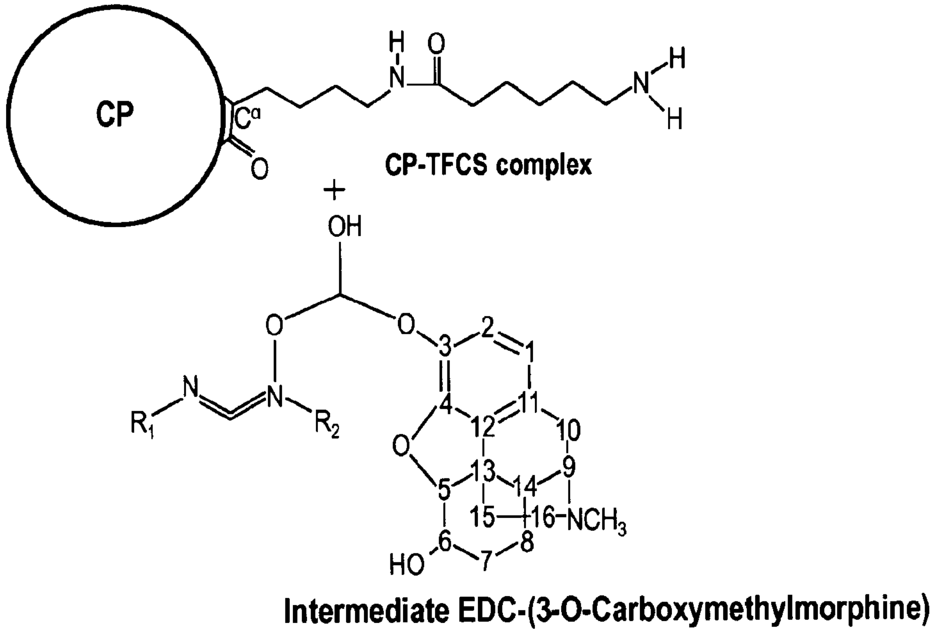
FIG. 12 depicts an alternate model of synthesizing an EDC-3-O-carboxymethylmorphine derivative.
Figure 12B:
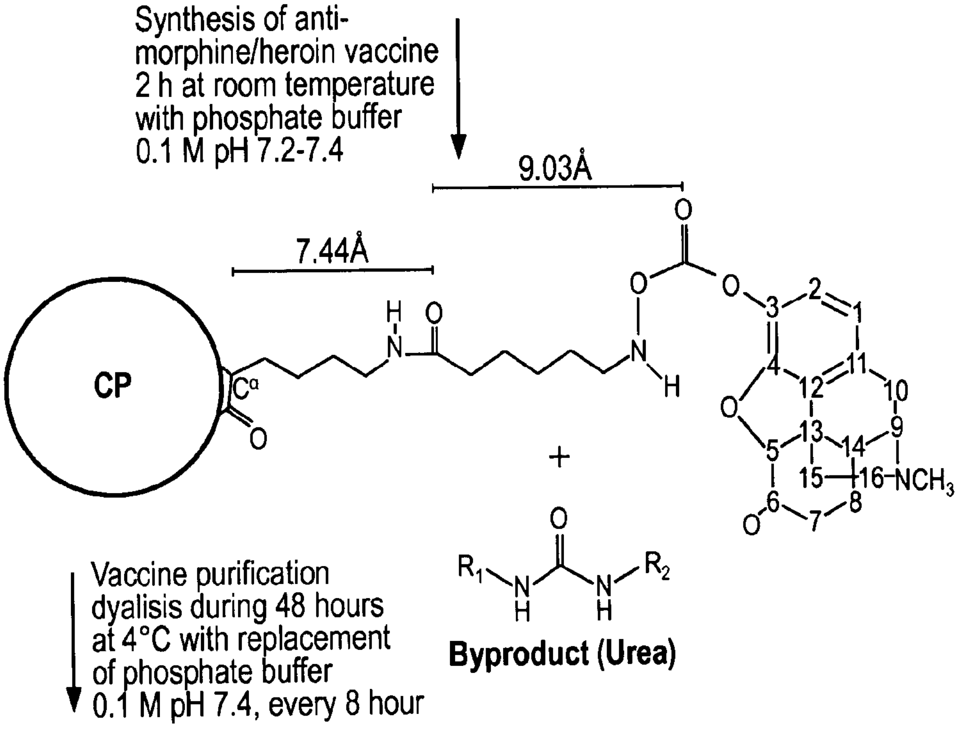

In addition to the synthetic, structural formulation, purification procedures, and therapeutic uses of the disclosed invention of the bivalent vaccine against morphine-heroin addiction, it is also revealed a complementary synthetic and purification procedures of another structural formulation of this bivalent vaccine against morphine-heroin addiction. This additional structural formulation of an anti-morphine-heroin vaccine consists in the alternate synthesis of an EDC-3-O-carboxymethylmorphine derivative product, using same synthetic protocols and procedures previously reported in the literature (S. Spector and C. W. Parker, Science, 168:1347, 1970; S. J. Spector, J. Pharmacol. Exp. Ther, 178:253, 1971; H. Van Vunakis et al., J. Pharmacol. Exp. Ther, 180:514, 1972 and S. Gross et al., Immunochemistry 11:453-456, 1974). This EDC-3-O-carboxymethylmorphine derivative was also covalently linked to the tetanus toxoid-TFCS conjugate according to the synthetic procedures used to synthesize the structural formulation of the bivalent anti-morphine-heroin vaccine in the present invention, using the synthetic procedure as shown in FIG. 12.

a)

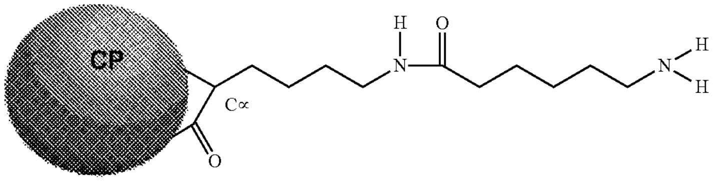

CP-TFCS complex

+

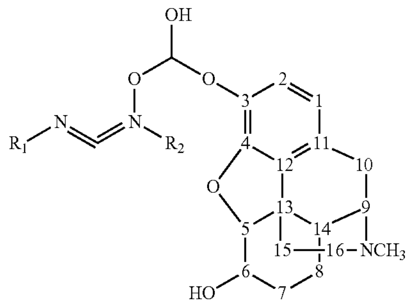

Intermediate EDC-(3-O-Carboxymethylmorphine)

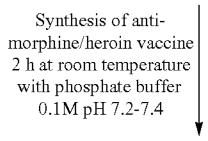

-continued b)

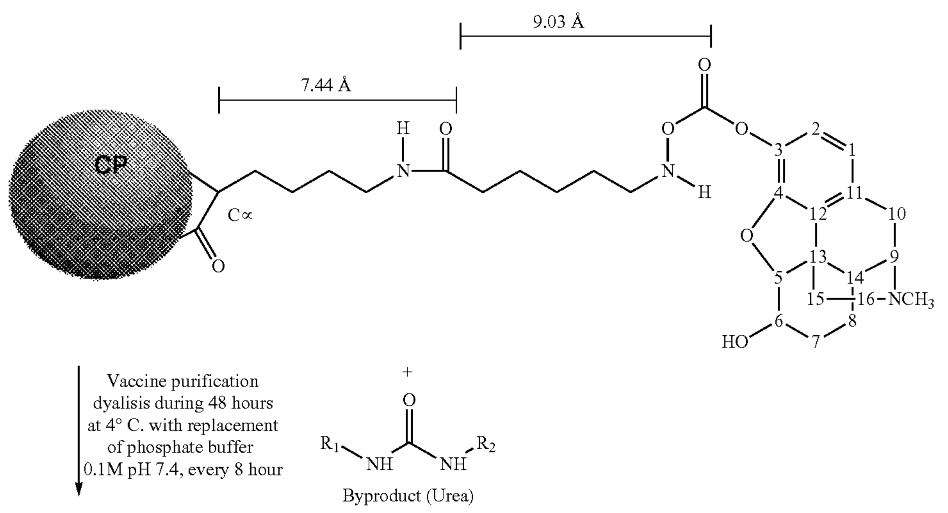

Figure 13:
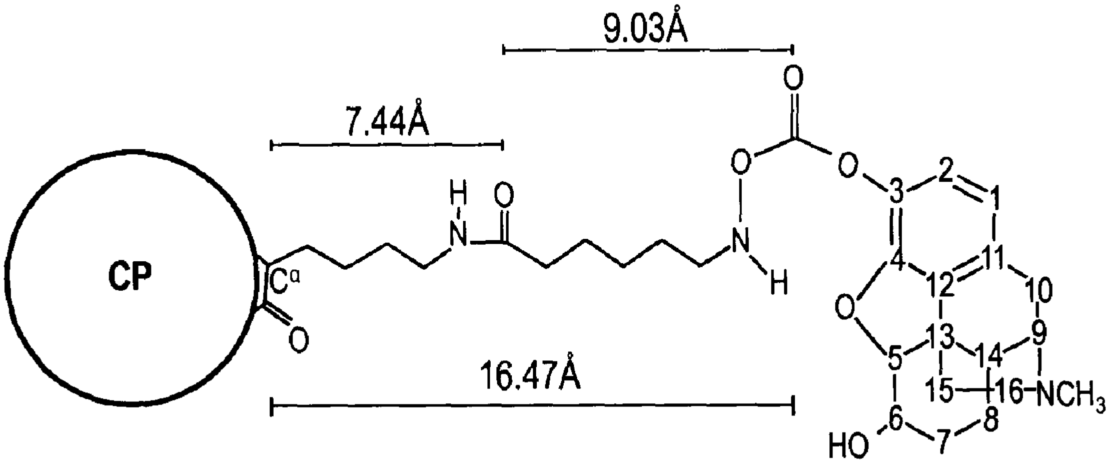
FIG. 13 depicts the molecular formular of an alternate bivalent anti-morphine-heroin vaccine.

This alternate model of the bivalent anti-morphine-heroin vaccine displays a different spacer-linker arm structure with a total molecular size of 16.47 Å, where the 9.03 Å right-hand segment comprise the hydrocarbonated backbone introduced by the TFCS reagent, linked through an amide covalent bond to the EDC-3-O-carboxymethyl residue in the phenantrenic ring structure of the morphine molecule. The 7.44 Å left-hand segment comprise the α-carbon atom and the four carbon atoms of the lateral chain of lysine residues of the tetanus toxoid, which have been covalently linked through the ε-amino group to the left-hand side end-segment of TFCS reagent, as depicted in the formula as shown in FIG. 13.

dated in active vaccination protocols in animal species, which include commercially available formulations, such as water-oil emulsions that may or may not contain *Mycobacterium tuberculosum* inactivated by heat exposure (Sigma-Aldrich), RIBI (RIBI Immunochem Research, Inc.) besides other formulations containing biodegradable polymers and liposomes (see review in J. Kohn et al., J. Immunol. Methods, vol. 95, pp 31-38, 1986).

After extensive decades of experimental research, the very few authorized and approved adjuvants used for human vaccination comprised formulations containing aluminum hydroxide. The preparation of a pharmaceutical composition

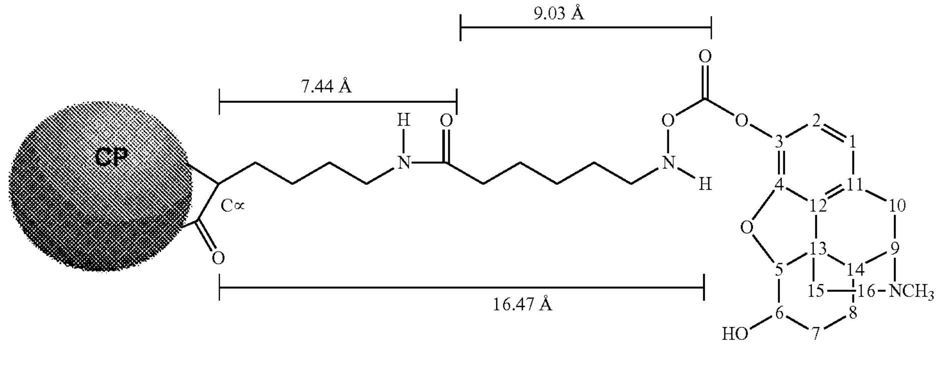

Adjuvants

Despite of high molecular mass and the multiplicity of immunogenic epitopes displayed by the immunoconjugates containing covalently linked haptens of low structural complexity, as shown by our novel vaccine model against morphine and heroin addiction, its administration to a subject requires the supplement of adjuvant compounds, known to strength the initial immune response (E. Harlow and D. Lane, Antibodies: A Laboratory Manual, Cold Spring Harbor Laboratory, New York, pp 96-97, 1988). In this context, adjuvants have the capability to induce a potent humoral and/or cellular immune response to large types of antigens which includes, carbohydrates, peptides and proteins. Therefore, several chemical formulations of adjuvants have been used and valior therapeutic formulation that includes the "bivalent vaccine against morphine and heroin addiction" in the present invention can be carried out using standard techniques handled by field experts, together with any of the accepted vehicles, auxiliaries and/or pharmaceutical excipients described in the art of the technique, including, with no limitation, different adjuvant substances. A typical dosification formulation of the bivalent vaccine against morphine-heroin addiction and adjuvant used for active vaccination protocols in both animal and humans, consist in the preparation of a mixed ratio of 1:2 (v:v) of the bivalent vaccine:aluminum hydroxide by mixing 1 ml of the vaccine resuspended in sterile deionized $H_2O$; with 2 ml of a stock solution of 45 mg/ml of aluminum hydroxide (Imject-R-Alum, Pierce) added by slow dripping (in no less than 3 minutes). The mixture of the reactants are incubated under slow and constant stirring for 1-2 hours at room temperature. The final concentration of aluminum hydroxide should not exceed 1.12-2.25 mg/100 μl in the reaction during the mixing process with the bivalent vaccine against morphine-heroin addiction. After the mixture has been completely stirred, the formulation of the bivalent anti-morphine-heroin vaccine/aluminum hydroxide adjuvant should be loaded into sterile plastic syringes, using the parenteral route (i.e., subcutaneous, intramuscular and intraperitoneal) as preferential administration routes to introduce the vaccine formulation into the host, with the exception of the intravenous route.

Other available immunogenic adjuvants that can be combined and administered with the present invention of the bivalent vaccine against morphine-heroin addiction includes a large group of compounds, such as aluminum phosphate, interferons, interleukins, polylactic acid esters, biodegradable copolymers consisting in polyglycolic acid esters, liposomes, bacterial membranes lipopolysaccharides, bacterial muropeptides and RIBI. These formulations and/or compositions adopt the pharmaceutical forms of injected solutions, suspensions, powders and similars compounds.

Active Immunization

The intramuscular route is the preferred parenteral route by means of which the present invention of the bivalent anti-morphine-heroin vaccine mixed with aluminum hydroxide adjuvant should be administered to subjects, although, other parentental routes, such as the subcutaneous and intraperitoneal, may be used for vaccination protocols. The present invention of bivalent vaccine against morphine-heroin addiction, or the pharmaceutical composition or therapeutical formulation containing this immunogenic vaccine preparation, should be administered using a therapeutically effective dose and a established dose-administration protocol/regimen just only in the abstinent and detoxified subject from their previous morphine and/or heroin addictive behavior. This protocol should always be adjusted according to the degree of both complaint and addiction of the individual. A typical active immunization schedule uses the intramuscular route to inoculate this vaccine formulation in a dose-unit of the haptenic drug-carrier protein conjugate of up to 1-2 mg/kg of the individual's body weight (i.e., male rats of 250-350 mg weight, Wistar or Sprague-Dawley strain). This priming inoculation must be subsequently followed by 3-6 reboosting periods, administered at 14-day intervals, by administering the same dose-unit of this vaccine formulation during reboosting. The active immunization in control subjects is carried out only with adjuvant (aluminum hydroxide) or with adjuvant plus carrier protein (aluminum hydroxide+tetanus toxoid). The serum obtained from vaccinated subjects should be sampled 10-12 days after each reboost using standard protocols and procedures previously reported (E. Harlow and D. Lane, Antibodies: A Laboratory Manual, Cold Spring Harbor Laboratory, New York, 1988) to monitor the humoral immune response against morphine and heroin, including to its endogenous metabolites. To achieve these experimental conditions, different vaccinated experimental animals were bled (100 μl/animal) and the sera fractions were obtained after collected samples were subjected to blood clotting for 24 hours at 4° C., followed by centrifugation of the clot/supernatant fraction at 14,000×g. The obtained serum fractions were immediately frozen at 20° C. until use.

Antibody capture ELISA immunoenzymatic assays were used to identify and monitor the humoral immune response against both opiate substances, after each reboost, according to the active immunization procedure described above. These results allowed to support the efficacy of our novel anti-morphine-heroin vaccine to induce a robust humoral immune response against these opiate compounds. Moreover, these results led to identification of the number of reboosts required to induce a humoral response with maximum and stable levels of serum antibodies against these opiate substances. Altogether, these experimental data were used to select and define candidate hyperimmune animals that were subsequently exposed to the immunoprotection protocol against these opiate substances using the rat behavioral model of the addictive intravenous opiate self-administration paradigm (see below FIGS. 6 and 7).

A typical immunoenzymatic procedure of antibody capture ELISA assay used to monitor the humoral immune response against morphine and heroin from the serum of actively vaccinated subjects with our therapeutic antimorphine-heroin vaccine formulation consists in the initial synthesis of the solid phase of the assay by enhancing the adsorption of 3-4 μg of the antigenic preparation of morphine-6-hemisuccinyl-BSA/well in 96-well plates (Immunolon I, Corning). The captured of anti-morphine/anti-heroin antibodies by the antigenic fraction absorbed onto the solid phase is carried out after a 6 h incubation period at room temperature of aliquots (50 μl/well) containing progressive serial dilution of antibodies obtained from immunized animals (i.e., 1:10, 1:100, 1:1,000, 1:10,000 and 1:1,000,000). Thereafter, the wells are extensively washed with a solution containing 1% BSA/0.3% Tween-20/PBS, pH 7.4, followed by 2-3 hours incubation period at room temperature with a secondary anti-IgG (H+L) rat antibody (Vector Laboratories) conjugated with horseradish peroxidase. After this incubation period, the wells are extensively washed to remove the excess of the unbound secondary antibody, followed by the detection of immunopositive signals/well using a chromogenic substrate (OPD, SIGMA). The assayed wells are exposed to spectrometric detection of the absorbance values at 490 nm of the antibody fraction captured by the antigenic solid phase using a microplate ELISA-detector system. The obtained spectrometric absorbance values reflect the amount of antibody captured by the antigenic solid phase. Thus, the final antibody titer values are estimated and expressed as the inverse value of the diluted fraction of antisera tested that gives 50% of the maximum absorbance response, using computer standarization procedures.

FIG. 1 shows a representative result of an antibody capture ELISA assay used to identify initially the efficacy of our novel bivalent vaccine against morphine-heroin addiction to induce a humoral immune response with high antibody titers (i.e., producing an average titer value of ≈1:100 000) against morphine, shortly after the second reboost in a group 10 sampled immunized animals. As shown in the figure, the concentration of reactive antibodies detected through its absorbance at 490 nm in the assay decreases proportionally to the serial dilution of the antisera.

Figure 2:
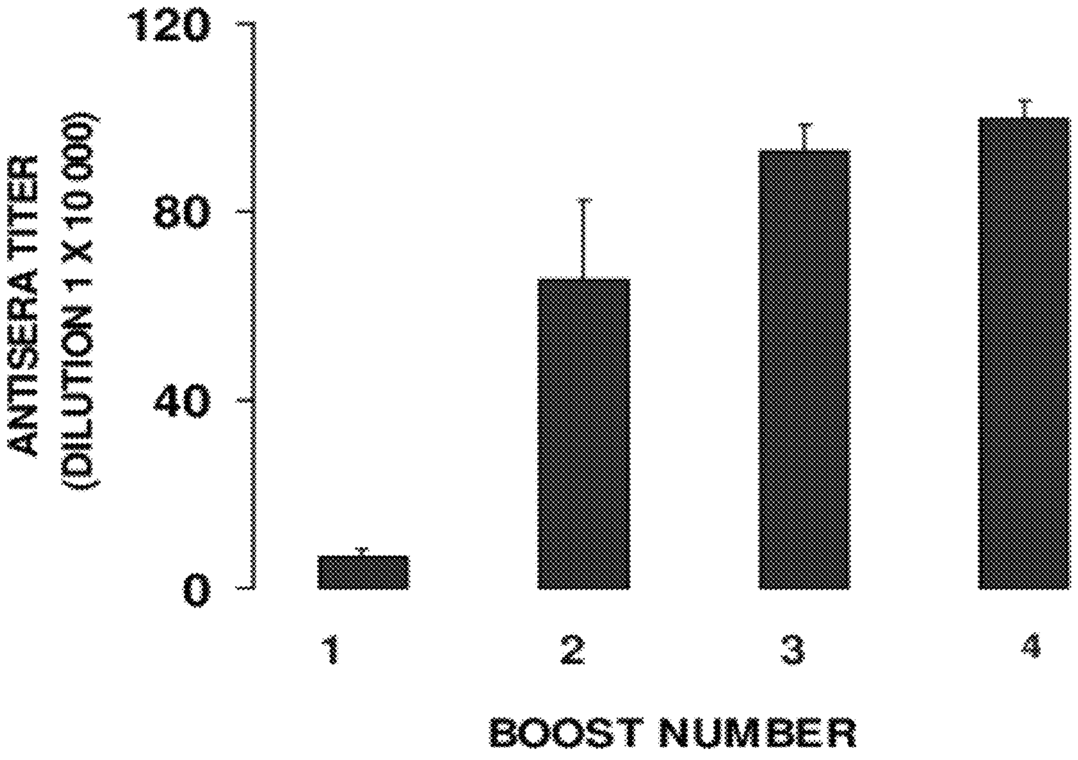
FIG. 2, shows the a representative plot which depicts the monitoring of the humoral immune response of serum titers of morphine/heroin antibodies in the rat, quantified through antibody capture ELISA assays, along four consecutive reboosts with the novel tetanus toxoid-morphine during the active vaccination schedule in the rat.

FIG. 2 depicts a representative result of an antibody capture ELISA assay for monitoring the time-course of serum titers of antibodies for morphine-heroin after reboosting animals (1-7 reboosts) periodically with the bivalent vaccine preparation against morphine-heroin addiction. After priming rats (first inoculation) with this novel therapeutic formulation of the bivalent vaccine against morphine-heroin addiction, the serum antibody titers against these opiate substances were monitored 10-12 days after each reboost (from 4-7). As shown in the figure, a progressive increase in antibody concentration against these opiate substances was obtained up to the fourth reimmunization period, where 10 actively vaccinated animals exhibited mean titer values ranging from 1:800,000-1:1000,000. However, the subsequent reimmunizations with the morphine-heroin immunogen (from the 5-7th) were not effective in inducing significant increasing antibody titers in animals considered hyperimmune to these opiate drugs (data no shown in the figure). This latter result postulates the use of short-term active immunization protocols with our novel therapeutic anti-morphine-heroin vaccine formulation to reach a maximum humoral immune response against both opiate substances.

Figure 3:
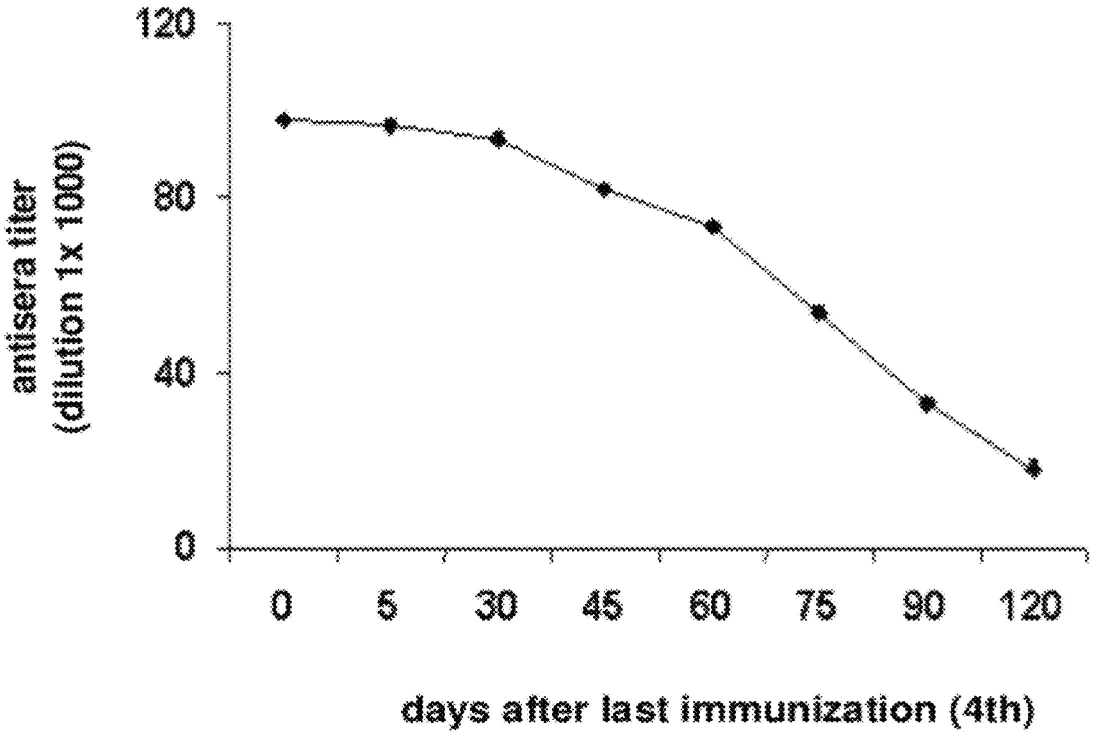
FIG. 3, shows a representative plot of antibody capture immunoenzymatic ELISA assays used to monitor the behavior of the humoral immune response after the last re-immunization (fourth) with the new tetanus toxoid-morphine immunogen.

One of the central goals to be reach by every novel model of therapeutic vaccines when used in active immunization protocols, is their capability to induce a robust and stable over time humoral and/or cellular immune response established with long-term immune memory. In this context, the FIG. 3 is a plot of representative data showing a temporary decrease of the humoral immune response of antibodies against morphine-heroin seen after the fourth reimmunization in actively vaccinated subjects (n=10) with our novel therapeutic vaccine formulation. Noteworthy is the fact that non-rebbosted hyperimmune animals, show a progressive time-course decrease of antibody titers along a 120 day period. The initial antibody titer obtained after the last re-immunization (which averaged between 1:800,000-1:1000,000) showed a significant decreased of about 40-50 times, reaching an average minimum titer value of 1:20,000 at the end of this period of time. These data show and support the hypothesis that active immunization with our novel therapeutic anti-morphine-heroin vaccine formulation is able to induce a classical humoral immune response reaching stable antibody titers, at least after the fourth re-immunization. This evidence is strongly supported by the experimental data obtained from antibody capture ELISA as depicted in FIG. 4, which shows that a long-term immune memory response against these two opiate substances has been established after the fourth reboost. This figure shows the average values of serum antibody titers of ten experimental subjects exposed to a subsequent reboost with the bivalent vaccine after completing a long-term non-reboosting period of six months from the last re-immunization ($4^{th}$). As shown in the figure, active re-immunization with the present invention of the therapeutic anti-morphine-heroin vaccine formulation induced a rapid and stable recovery of the pre-existing maximum levels of antibody titers against these opiate substances (i.e. usually within the first 5-10 days after reboosting) in non re-immunized hyperimmune animals. It is worth to note the similar time-course decrement of antibody titers shown after the fourth reboost (see FIG. 3) in non-vaccinated hyperimmune animals (i.e., after challenging animals with the latter vaccine reboost, the maximum titer levels were reached 15-20 days after reboosting, followed a slow and progressive linear decreased during the next 30 days, reaching the lowest levels of detected antibody titers up to 120 days, data not shown in figure).

Once the efficacy of our novel therapeutic formulation of an anti-morphine-heroin vaccine was evaluated and validated in active vaccination protocols by showing its capability to generate a robust humoral immune response characterized by high and sustained serum antibodies titers against these opiate substances, additional immunoenzymatic competitive ELISA assays were designed and developed to evaluate and identify the specificity of the anti-morphine-heroin antibodies.

This competitive ELISA assay used to evaluate the antibody specificity is based on the same experimental design used for the aforementioned non-competitive ELISA assays. The difference to the competitive ELISA assays consists in a preadsorption step of the specific antisera from hyperimmune animals using different concentration (i.e. that range in the nM-μM range) of potential competitive antigens potentially cross-recognized by the anti-morphine antibodies. These competitive antigens included morphine as the positive control substance in addition to the three main endogenous metabolites of morphine and heroin (e.g., 6-monoacetylmorphine, morphine-3-glucuronide and morphine-6-glucuronide) shown to display opiate-reinforcing properties, and heroin, as the synthetic structural analogue of morphine, shown to exhibit at least a an order of magnitude higher in its opiate-reinforcing properties at equivalent dose, than its natural opiate ortholog, morphine. Two other representative endogenous opioid peptides produced in the CNS of mammals, such as leucine-enkephalin and β-endorphin, were also included as competitive antigens in this assay. Furthermore, this assay also included pharmacological active competitive antagonists compounds for opioid receptors, such as naltrexone, a commonly used substance in the maintenance of abstinence from heroin addiction in the humans.

As this assay is based in the detection of positive signals originated from the absorbance emitted from the reacting wells when exposed to the microplate ELISA detector system at 490 nm, wells exhibiting an absence of significant signals at this wavelength (490 nm) suggest the lack of specific antibodies captured by the solid phase adsorbed antigen (which in our case was the morphine-6-hemisuccinyl-BSA conjugate). If occurring, this latter experimental condition would indicate that serum antibodies generated by active vaccination with our novel anti-morphine-heroin vaccine formulation would display potential cross-recognition for some of the competitive antigens used in the assay.

The representative data depicted in FIG. 5 illustrate a competitive immunoenzymatic ELISA assay, which shows the equivalent specificity of the serum antibodies to cross-recognize morphine and heroin (note that both competition curves display similar competitive morphine and heroin doses in the range of up to 0.6-0.8 μM at the $IC_{50}$ reference values). Additionally, these assays also show the capability of such anti-morphine-heroin serum antibodies to cross-recognize different biotransformation metabolites from these opiate substances (i.e., 6-monoacetyl-morphine, morphine-3-glucuronide and morphine-6-glucuronide). Furthermore, no cross-recognition to other substances such endogenous opiate peptides and the opiate receptor antagonist naltrexone was observed in same assays. Collectively, these results make feasible to propose the potential lack of immunological interference of this immunogen in active vaccination protocols when it could be used in humans treated with classical anti-addictive therapies using morphine structurally dissimilar opiate medications opioid such as naltrexone, naloxone, methadone and buprenorphine. Moreover, it may be assumed that our new therapeutic vaccine formulation against morphine-heroin addiction is not able to generate an autoimmune response, because the antibodies generated by this vaccine are not able to cross-recognize endogenous opioid peptides (i.e., leucine-enkephalin and β-endorphin) that besides to be synthesized in the brain in hyperimmune vaccinated animals including humans, they do participate in the regulation of a multiple array of physiological activities and processing of a wide range of brain functions in the CNS of mammals.

Evaluation and Validation of the Efficacy of the Present Invention of the Therapeutic Bivalent Vaccine Formulation Against Morphine-Heroin Addiction After showing the validation of the efficacy of the present therapeutic bivalent anti-morphine-heroin vaccine formulation to confer hyperimmunicity against morphine and heroin with an enhanced long-term immune memory response, through the generation of high and sustained serum titers of specific reacting antibodies against these opiate drugs and their endogenous metabolites in immunized subjects, we decided to explore the immunoprotective effects of the present therapeutic vaccine formulation against the re-acquisition of addictive intake behavior in hyperimmune animals detoxified and abstinent from addiction to these opiates. In this context, tested hyperimmune against morphine/heroin animals were exposed to operant behavioral tests using the intravenous drug self-administration paradigm for both morphine and heroin. These pharmacological paradigms used in the animal model of the rat were implemented from related pharmacological paradigms previously reported by several research groups (J. M. Van Ree et al., J. Pharm. Exp. Ther., 204 (3): 547-557, 1978; J. M. Van Ree and D. de Wied, Life Sci. 21:315-320, 1977; T. J. Martin et al., J. Pharmacol. Exp. Ther. 272:1135-1140, 1995; P. Hyytiä et al., Psychopharmacology, 125:248-254, 1996; T. J. Martin et al., Brain Res. 755:313-318, 1997; C. W. Hutto, Jr. and W. F. Crowder, Pharmacol. Biochem. Behav. 58(1):133-140, 1997; R. Ranaldi and E. Munn, Neuroreport, 9:2463-2466, 1998; S. Martin et al., Brain Res. 821:350-355, 1999; I. M. Maisonneuve and S. D. Glick, Eur. J. Pharmacol, 383:15-21. 1999; S. D. Comer et al., Psychopharmacology, 143327-338, 1999; S. Semenova et al., Eur. J. Pharmacol. 378:1-8, 1999; M. R. A. Carrera et al., Psychopharmacology, 144:111-120, 1999; Z-X. Xi and E. A. Stein, J. Pharm. Exp. Ther. 290:1369-1374, 1999 and L. J. Sim-Selley et al., J. Neurosci. 20(12):4555-4562, 2000).

The pharmacological models of intravenous self-administration paradigms of both morphine and heroin in the rodent have been widely used to explore the neurobiological mechanisms by which these opiate produced their drug-reinforcing properties. Additionally, these models have been also used to evaluate the anti-addictive effects of therapeutic compounds such as methadone, naloxone and naltrexone. Moreover, these pharmacological paradigms are extremely useful to evaluate the motivational and drug-reinforcing responses, independently from the direct pharmacological effects produced by these opiate drugs in the nervous system (i.e, psychomotor activation) when proper protocols are employed during the pharmacological self-administration of these substances. Therefore, in order to evaluate and validate the immunoprotective effects against morphine-heroin addiction confered by the present invention of the therapeutic bivalent anti-morphine-heroin vaccine formulation, our laboratory designed, developed and validated an intravenous drug self-administration paradigm for these two opiate substances in the animal model of the rat.

a). Development, Implementation and Validation of the Intravenous Self-Administration Paradigm of Morphine and Heroin in the Animal Model of the Rat The pharmacological model of the intravenous morphine/heroin self-administration paradigm in the rat was standardized from several protocols previously reported by different groups (J. M. Van Ree et al, J. Pharm Exp. Ther., 204 (3):547-557, 1978; J. M. Van Ree and D. of Wied, Life Sci. 21:315-320, 1977; T. J. Martin et al., J. Pharmacol. Exp. Ther. 272: 1135-1140, 1995; P. Hyytiä et al., Psychopharmacology, 125: 248-254, 1996; T. J. Martin et al., Brain Res. 755:313-318, 1997; C. W. Hutto, Jr. and W. F. Crowder, Pharmacol. Biochem. Behav. 58(1):133-140, 1997; R. Ranaldi and E. Munn, Neuroreport, 9:2463-2466, 1998; S. Martin et al., Brain Res. 821:350-355, 1999; I. M. Maisonneuve and S. D. Glick, Eur. J. Pharmacol, 383:15-21. 1999; S. D. Comer et al., Psychopharmacology, 143327-338, 1999; S. Semenova et al., Eur. J. Pharmacol. 378:1-8, 1999; M. R. A. Carrera et al, Psychopharmacology, 144:111-120, 1999; Z-X. Xi and E. A. Stein, J. Pharm. Exp. Ther. 290:1369-1374, 1999 and L. J. Sim-Selley et al., J. Neurosci. 20(12):4555-4562, 2000). Basically, this pharmacological model consists in using surgically implanted animals with teflon sterile catheters placed into the right or left external jugular vein to opiate intravenous self-administration paradigms using morphine and heroin as drug-reinforcers, during 4 h/daily sessions, inside operant conditioning Skinner boxes, controlled by the observer using computerized signals. In this context, the intravenous infusion of a complete "dose-unit" of each of these two opiate substances is established by the fixed number of operant lever responses made by the animal on a retractile lever (placed on the front panel of Skinner boxes) at specified time intervals. For example, the infusion of a dose-unit of morphine (i.e. 1900 μg/0.2 ml/kg of weight) and heroin (60 μg/0.2 ml/kg) are carried out when the animal completes a fixed number of lever responses (i.e. 1, 3, 5, 10) after a defined time intervals (i.e., 20, 40, 80 seconds), time at which the retractile lever is inactive. Thus, under this pharmacological conditions, one can evaluate the drug-intake behavior responses, by estimating in the 4 hour/daily sessions the total number of opiate infusions made by the animal. Also included in the analyses are the measurements of drug-seeking behavior responses by estimating the total number of lever retractions occurring at the time-intervals, when the retractile lever is inabilitated. Under these experimental conditions, trained animals established the amount of opiate drug require to be self-administered. Thus far, this pharmacological paradigm allows to carry out quantitative and reproducible procedures used to estimate the accumulated doses of intravenously self-administered drug/animal/session/day, including the accumulated doses of self-administered drug/animal throughout the training schedule (i.e., accumulated data over 15, 30, 60 days). The capability of morphine and heroin to induce an operant behavioral response (i.e, manipulation of the retractile lever to produce a and/or drug-seeking behaviors) is defined as the reinforcing properties of each drug to discriminate the drug-associated stimulus. In this context, hiperimmune vaccinated animals with the bivalent vaccine of the present invention, with immune humoral responses of high and sustained anti-morphine-heroin serum antibody titers, should blunt or neutralize the drug-reinforcing properties induced by these opiate substances in the brain, when challenged to acquire the addictive intravenous self-administering behavior of either morphine or heroin. These animals should show a significant decrease of opiate drug-taking and drug-seeking behavioral responses due to the absence of reinforcing drug-associated stimuli.

In summary, this pharmacological model based on the intravenous opiate self-administration paradigm, allowed us to obtain and construct baselines of the operant drug-intake behavior in animals that consolidated addictive responses to both morphine and heroin. The pharmacological parameter concerning the opiate-intake behavioral responses to both morphine and heroin were obtained after comparing the self-infusion rates of these drugs in hyperimmune animals immunized with the therapeutic bivalent anti-morphine-heroin vaccine formulation of the present invention and control groups (non-immunized or immunized only with adjuvant and adjuvant plus carrier protein, see representative results in FIGS. 6 and 7).

1. Functional Development and Implementation of Skinner's Operant Boxes.

The installation and functioning of eight Skinner's operant boxes (aluminum and transparent acrylic) designed for intravenous self-administration of liquids and drugs in the rat animal model were developed according to the operating standards recommended by the manufacturer (Operant Behavior Conditioning Systems for lab animals, TSE Systems, Hamburg, Germany).

2. Development of Conditioning Learning Training Paradigms for Lever Press and Food Reward.

Wistar male rats (260-320 g) were trained to localize and press retractile levers within the operant Skinner boxes, and for each lever press, animals were rewarded with a maximum of 200 food pellets (45 mg) (Noyes Traditional Food Precision Pellets; Research Diets, Inc., Lancaster, N.H.) during 5-7 days in a 4 h training sessions. Under these experimental conditions, animals were conditioned to obtained food-reward (reinforcing stimulus) each time they pressed the retractile lever [fixed reinforcement protocol 1(FR1)], upon exposure of a cue light stimulus (conditioned stimulus), controlled online by software (TSE, OBS system) during daily 4 h sessions for a period of 5-7 days. After this training period, the duration of the sessions were shortened to 30 minutes, increasing the time-out intervals from 5 (TO-5) to 20 sec (TO-20), time at which retractile levers were inabilitated during the next following 3-5 days. Thus, animals were trained to complete their lever responses by obtaining only 50 pellets under a fixed reinforcement schedule (FR1,T0-20 sec) in a daily 30-minute sessions. Animals succeeding in this behavioral conditioning training, were returned to their individual home cages, under restrict diet (16-20 gr food pellets/day), and subsequently exposed to the surgical implantation of Teflon intravenous catheters into the external jugular vein, so as to initiate the experimental procedures of immunoprotection against morphine/heroin addiction when exposed to the intravenous opiate self-administration paradigms.

3. Surgical Implantation of Sterile Catheters into the External Jugular Veins.

Experimental animals trained for lever press and food reward, using the operant conditioning behavior described above, were subjected to general anesthesia and surgical aseptic conditions for the surgical implantation of teflon sterile catheters within the right or left external jugular veins. The whole surgical procedure was performed according to standard surgical protocols described by K. M. Kantak et al. (Psychopharmacology, 148:251-262, 2000). After surgery, animals were returned to their home-cages and the functional viability of the implanted catheters were checked in a daily basis by infusing saline solution and antibiotics [5% Enrofloxacyn (0.50 mg/kg); Gentamicyn-Super 5 mg/kg). After seven days of post-surgical recovery, animals were then subjected to the pharmacological paradigms of intravenous self-administration of both morphine and heroin.

4. Development and Establishment of Baseline Responses of Intravenously Self-Administered Morphine and Heroin.

The functional viability of implanted catheters in post-surgically recovered animals was verified prior to exposing animals to 4 hour/daily sessions of our intravenous morphine and heroin self-administration paradigm. Initially, separate groups of animals were exposed to the contingent self-administration of a fixed dose-unit of morphine (1900 μg/kg/0.2 ml saline) during 10 seconds injection) or heroin (60 μg/kg/0.2 ml of saline/10 seconds injection) following a fixed reinforcement schedule (FR1) TO-20 seconds, during 4 hour-daily sessions for 5-7 consecutive days. The difference of these reinforcing dose-unit values between morphine and heroin was based on data previously reported in the literature (J. M. Van Ree et al, J. Phar. Exp. Ther. 204(3):547-557, 1977 and C. W. Hutto, Hr. and W. F. Crowder, Phar. Biochem. Behav. 58(1):133-140, 1997) which showed that a morphine:heroin dose-ratio relationship of 32:1, produces equal choice on the self-infusion of these opiate substances when self-administered by the rat under this experimental conditions. This training period led animals to acquire stable baseline responses on the contingent self-administration of these opiates, over an additional training period of 7-10 days. Under these protocol conditions, trained animals produced average baseline infusion-responses of 25±3 and 20±5 during self-administration of the fixed dose-units of both heroin and morphine, respectively. Baseline self-infusion responses to these two drugs were considered established and consolidated when the variability coefficient values varied no more than 10% for each drug along self-infusion sessions, for at least five consecutive experimental days. Once the initial baseline self-infusion responses to both morphine and heroin were achieved, the initial extinction phase was carried out by substituting the opiate substances for vehicle solution (i.e. vehicle solution=saline 0.9% NaCl in sterile deionized $H_2O$) during the next following 3-5 days, just after baseline self-infusion responses to both opiates were established. The extinction responses to self-infusion of both morphine and heroin responses achieved by surgically implanted animals were defined after achieving a mean average number of extinction responses/session/day of 3±2 to the self-administered vehicle solution, in groups of animals trained to self-administered either morphine or heroin that consolidated an initial phase of baseline responses as mentioned above. To consolidate the opiate self-administration behavior responses to both morphine and heroin, two subsequent re-acquisition-extinction cycles of opiate self-administration were performed. In this experimental context, fifteen days after obtaining the average baseline responses of the extinction phase to the opiate self-administration paradigm, we evaluated the antagonism effect of the anti-morphine-heroin serum antibodies on the re-acquisition of the self-infusion addictive behavior responses to both opiate substances in hyperimmune animals (trained to self-administer these opiate substances) after being actively immunized with the therapeutic bivalent vaccine formulation against morphine-heroin addiction, using the vaccination/immunization protocol disclosed in the present invention.

5. Characterization of the Immunoprotective Effect Against Morphine-Heroin Addiction Induced by Active Immunization with the Anti-Morphine-Heroin Vaccine of the Present Invention Different groups of animals trained to self-administered morphine and heroin which established baseline self-infusions of these opiate drugs where actively vaccinated with either the therapeutic morphine-heroin bivalent vaccine formulation of the present invention or control compounds (i.e., aluminum hydroxide used as co-adjuvant and this co-adjuvant plus tetanus toxoid used as the carrier protein) following the same immunization protocol disclosed in the present invention. Once the humoral immune response against these two drugs (see FIGS. 1, 2, 3 and 4) was established in hyperimmune vaccinated animals, they were then re-exposed to the intravenous self-administration paradigm with both morphine and heroin, so as to assess the immunoprotective responses against these opiate drugs by measuring the number of complete self-infusion responses (drug-intake behavior) throughout 15-20 consecutive 4 hour-daily sessions. Same studies were carried out in the control animal groups, which received either the adjuvant alone or the adjuvant plus the carrier protein.

Data obtained were expressed as the mean average of accumulated number of complete self-infusion responses/day/in the experimental vaccinated group during 15-20 daily sessions, and assayed to evaluate the immunoprotective effect. The statistical analysis of data was performed by variance analysis (ANOVA), followed by a Newman-Keuls test for post-hoc comparison analysis.

Under this experimental context, tested groups included, hyperimmune animals against morphine-heroin (CP-MORPHINE, n=8) and control groups immunized with either aluminum hydroxide adjuvant (ALUM, n=8) or with the carrier protein plus adjuvant (CP+ALUM, n=8). All of them received same dose-unit of heroin or morphine during the intravenous self-administration paradigm as disclosed previously in the present invention. The results showing the average baseline responses (values) of the number of self-infusions achieved for each self-administered opiate substance, as well as the self-administered control vehicle (i.e., saline) along the 15-20 consecutive, 4 hour-daily sessions, are shown in FIGS. 6 and 7.

FIG. 6, depicts the immunoprotective effect induced by active vaccination with the therapeutic anti-morphine-heroin bivalent vaccine formulation of the present invention against the intravenous morphine self-administration behavior in the animal model of the rat. The group of rats immunized with the vaccine of the present invention, and the control groups, immunized with adjuvant or with adjuvant plus carrier protein were exposed to the morphine self-administration paradigm. Control animals that received only aluminum hydroxide (ALUM) as immunogen did not show significant changes with regard to the average responses of self-infusion of morphine/session (17±4, S.E.M.) compared to the pre-immunization average responses in control animals (18±5, S.E.M.). Conversely, animals vaccinated with the immunogenic morphine preparation (CP-morphine) showed a significant reduction in the average number of heroin self-infusions/session (4±3, S.E.M., $p<0.005$) compared to animals immunized with adjuvant (ALUM) or with adjuvant plus carrier protein (CP-alone+ALUM). It is worth to note the similar pattern of the mean average of self-infusion responses obtained with saline (control vehicle) achieved by animals immunized with these three different vaccine preparations (3±2 with ALUM, 3±2 with ALUM+CP; and 3±2 with the anti-morphine-heroin bivalent vaccine of the present invention).

FIG. 7, depicts the immunoprotective effect of the active vaccination with the therapeutic anti-morphine-heroin bivalent vaccine formulation of the present invention against the intravenous heroin self-administration behavior in the animal model of the rodent. The group of rats immunized with the present vaccine and the control groups immunized with adjuvant and/or with adjuvant plus carrier protein were exposed to the pharmacological paradigms of heroin self-administration. The control animals that received only aluminum hydroxide (ALUM) as immunogen did not show significant differences with regard to the mean average of heroin self-infusion responses/session (24±4, S.E.M.) when compared to the pre-immunization average responses (21±3, S.E.M.) obtained in control animals. Conversely, animals vaccinated with the immunogenic preparation of morphine (CP-morphine) exhibited a significant reduction in the average number of heroin self-infusions/session (6±2, S.E.M, $p<0.005$) compared to the animals immunized with adjuvant (ALUM) or with adjuvant plus the carrier protein (CP-alone+ALUM). Moreover, the average number of saline (control vehicle) self-infusions reached by animals immunized with these three vaccine preparations (3±2 in the group of animals immunized with ALUM; 2±3 in the group of animals immunized with ALUM+CP; and 3±1 in the group of animals immunized with the anti-morphine-heroin bivalent vaccine of the present invention) were very similar.

Finally, the application of this kind of therapeutic strategies is being evaluated for its future application in human subjects that exhibit serious addictive problems to both morphine and heroin.

Quite obvious to personal skilled in these techniques, that other available variations, not specifically presented in the text above, may nevertheless be proposed within the scope of the present invention, and thus, they are included under the protection of this invent. Thus, the present invention is not just limited to the description of the specific modalities presented as described above in the text, but clearly depicted in the following patent claims.

The invention claimed is:

1. A bivalent immunogenic composition comprising a carrier protein ("CP") and a morphinic product, wherein the CP and the morphinic product are connected by a spacer-linker arm, and wherein the immunogenic composition has one of the following structural formulas:

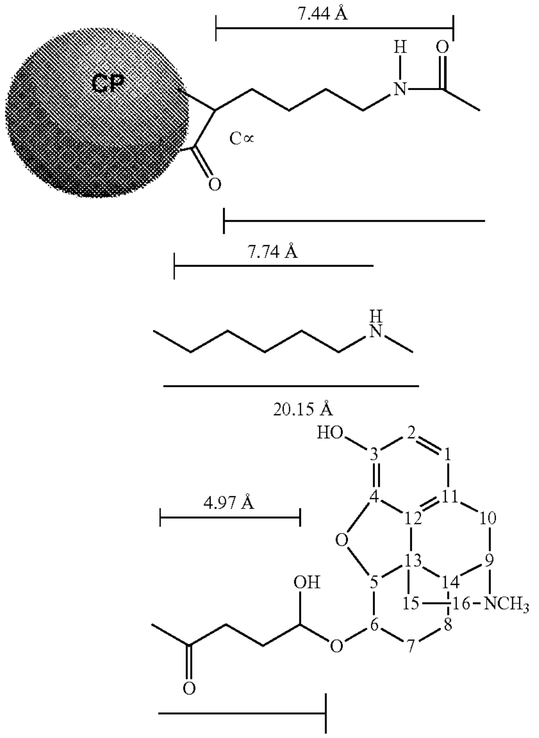

or

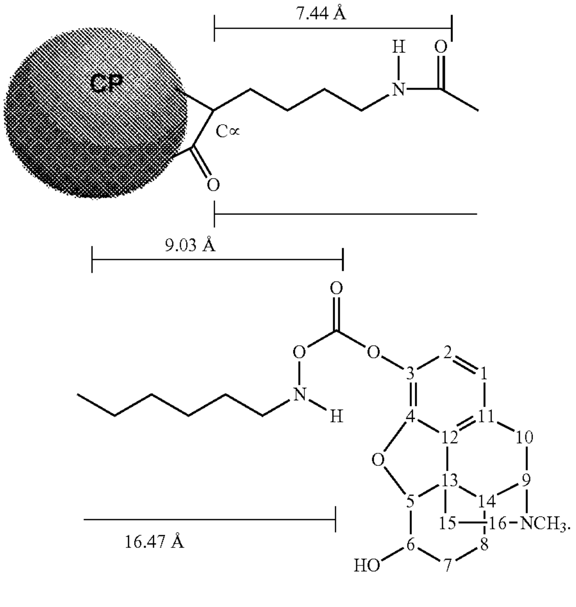

2. The immunogenic composition of claim 1, which is capable of enhancing a humoral immune response.

3. The immunogenic composition of claim 1, wherein the carrier protein is selected from the group consisting of tetanus toxoid, ovalbumin, rabbit, bovine, goat, horse, donkey serum albumin, human serum albumin, thyroglobulin, fibrinogen, KLH, goat erythrocyte membranes, flagellin, diphtheria toxins, cholera toxins, and botulinic toxins.

4. The immunogenic composition of claim 2, wherein the carrier protein is tetanus toxoid.

5. The immunogenic composition of claim 1, further comprising one or more pharmaceutically acceptable adjuvants or pharmacological agents.

6. The immunogenic composition of claim 5, wherein the pharmaceutically acceptable adjuvant is selected from the group consisting of aluminum hydroxide, aluminum phosphate, interferons, interleukins, polylactic acid esters, biodegradable copolymers, polyglycolic acid esters, liposomes, bacterial membrane lipopolysaccharides, bacterial muropeptides, and RIBI.

7. The immunogenic composition of claim 5, wherein the pharmacological agent is selected from the group consisting of naltrexone, naloxone, methadone, and buprenorphine.

8. The immunogenic composition of claim 5, which can be administered parenterally.

9. The immunogenic composition of claim 4, prepared according to the following steps;

a) reacting 100 mg (0.5 mM) of tetanus toxoid dissolved in 4 ml of a phosphate buffer solution/0.15 mM NaCl, pH 7.2 with 50 μl of a N (ϵ-trifluoracetylcaproyloxy)-succinimide-ester ("TFCS") stock solution containing 10-20% DMSO and 90-80% deionized $H_2O$, to begin formation of the intermediate conjugate;

b) obtaining a final tetanus toxoid concentration of 6.7 mM and 0.5-1% of DMSO;

c) obtaining a final dilution of 1:10-20 (v:v) of the initial DMSO concentration between tetanus toxoid and TFCS;

d) incubating the contents of step c) for up to 60-90 minutes at room temperature, wherein synthesis of the CP-TFCS occurs, and wherein TFCS still preserves a reactive amino protected by a protecting trifluoroacetyl chemical group;

e) incubating the CP-TFCS for 2-3 hours at room temperature and adjusting the pH to 8-8.5, with a concentrated 10N NaOH solution to enhance the protected trifluoroacetyl group in TFCS to be hydrolyzed, so as to generate free reactive amine groups in the CP-TFCS;

(f) reacting the morphinic product, EDC-(morphine-6-hemisuccinate) or EDC-3-O-carboxymethyl-morphine, with the CP-TFCS, wherein the reaction is carried out in a stoichiometric ratio by reacting mol:mol, 100 μmol of EDC-(M-6-H) per each 0.07 μmol of active free amino groups of the CP-TFCS; and (g) incubating the reactants obtained in step f) 2-3 hours at room temperature under slow and constant stirring to form the immunogenic composition.

10. The process according to claim 9, further comprising the step of purifying the CP-TFCS by dialysis.

11. A method of inducing or enhancing a humoral immune response by administering to a subject the immunogenic composition of claim 1.

12. The method of claim 11, wherein the immune response is characterized by circulating polyclonal antibodies with equivalent specificities to morphine/heroin metabolites.

13. The method of claim 11, where the initial administration is followed by 3-6 administrations at 14-day intervals at the same initial dose.

14. The method of claim 11, where the subject is human.

* * * * *